(12) United States Patent
Wagner et al.

(10) Patent No.: US 9,778,167 B2
(45) Date of Patent: *Oct. 3, 2017

(54) MOTION MODULATION FLUIDIC ANALYZER SYSTEM

(71) Applicant: Redshift Bioanalytics, Inc., Burlington, MA (US)

(72) Inventors: Matthias Wagner, Cambridge, MA (US); Charles McAllister Marshall, North Andover, MA (US); Donald Kuehl, Windham, NH (US); Jeffrey Guasto, Chestnut Hill, MA (US)

(73) Assignee: Redshift Bioanalytics, Inc., Burlington, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/175,709

(22) Filed: Jun. 7, 2016

(65) Prior Publication Data

US 2017/0030823 A1 Feb. 2, 2017

Related U.S. Application Data

(63) Continuation of application No. 14/693,301, filed on Apr. 22, 2015, now Pat. No. 9,377,400, which is a (Continued)

(51) Int. Cl.
*G01N 21/00* (2006.01)
*G01N 15/14* (2006.01)
(Continued)

(52) U.S. Cl.
CPC ..... *G01N 15/1436* (2013.01); *G01N 15/0205* (2013.01); *G01N 15/1404* (2013.01); (Continued)

(58) Field of Classification Search
CPC .... G01N 21/39; G01N 21/05; G01N 21/0332; G01N 21/3577; G01N 2021/399; G01N 2201/0612; G01N 15/1434; G01N 15/147
(Continued)

(56) References Cited

U.S. PATENT DOCUMENTS 8,004,661 B2 * 8/2011 Luscher ............. G01N 15/1404
250/461.2
9,377,400 B2 * 6/2016 Wagner ................... G01N 21/39
(Continued)

*Primary Examiner* — Hoa Pham
(74) *Attorney, Agent, or Firm* — BainwoodHuang

(57) ABSTRACT

A fluid analyzer includes an optical source and detector defining a beam path of an optical beam, and a fluid flow cell on the beam path defining an interrogation region in a fluid channel in which the optical beam interacts with fluids. One or more flow-control devices conduct a particle in a fluid through the fluid channel. A motion system moves the interrogation region relative to the fluid channel in response to a motion signal, and a controller (1) generates the motion signal having a time-varying characteristic, (2) samples an output signal from the optical detector at respective intervals of the motion signal during which the interrogation region contains and does not contain the particle, and (3) determines from output signal samples a measurement value indicative of an optically measured characteristic of the particle.

34 Claims, 19 Drawing Sheets

Related U.S. Application Data continuation-in-part of application No. 14/673,015, filed on Mar. 30, 2015, now Pat. No. 9,625,378, said application No. 14/693,301 is a continuation-in-part of application No. PCT/US2015/023324, filed on Mar. 30, 2015.

(60) Provisional application No. 61/982,470, filed on Apr. 22, 2014, provisional application No. 61/972,823, filed on Mar. 31, 2014, provisional application No. 62/039,666, filed on Aug. 20, 2014, provisional application No. 62/074,916, filed on Nov. 4, 2014.

(51) Int. Cl.
| | |
|---|---|
| *G01N 21/39* | (2006.01) |
| *G01N 21/05* | (2006.01) |
| *G01N 21/03* | (2006.01) |
| *G01N 21/3577* | (2014.01) |
| *G01N 21/85* | (2006.01) |
| *G01N 15/02* | (2006.01) |
| *G01N 21/53* | (2006.01) |

(52) U.S. Cl.
CPC ..... *G01N 15/1484* (2013.01); *G01N 21/0332* (2013.01); *G01N 21/05* (2013.01); *G01N 21/3577* (2013.01); *G01N 21/39* (2013.01); *G01N 21/532* (2013.01); *G01N 21/85* (2013.01); *G01N 2021/399* (2013.01); *G01N 2201/0612* (2013.01); *G01N 2201/10* (2013.01)

(58) Field of Classification Search
USPC ............... 356/244, 246, 335–343, 432–440; 250/338.1, 339.07, 338.5, 339.11, 343
See application file for complete search history.

(56) References Cited

U.S. PATENT DOCUMENTS

2011/0134426 A1\* 6/2011 Kaduchak .......... G01N 15/1404
356/337
2017/0016813 A1\* 1/2017 Wagner .............. G01N 21/3577

\* cited by examiner

MOTION MODULATION FLUIDIC ANALYZER SYSTEM

BACKGROUND

Infrared spectroscopy is a valuable, well-known tool for chemical characterization of gaseous, liquid and solid substances because compounds have distinct absorption "fingerprints" in the mid-infrared region, with absorption bands corresponding to vibrational energies of molecular bonds. In theory, infrared spectroscopy should be a very valuable tool for analyzing liquid samples for applications including, but not limited to: medical liquid analysis (blood, urine, saliva, etc.) for diagnostics or substance detection; industrial or food/beverage process control; and pollutant detection.

A major barrier to broader application of infrared spectroscopy to liquid samples has been the high inherent absorption of many liquids in the infrared. For example, water has strong infrared absorption, making analysis of aqueous solutions difficult. A number of tools have been developed to circumvent this issue, for example: the use of attenuated total reflection (ATR) prisms and other surface-grazing optical techniques; drying of samples before analysis; and the use of liquid-liquid extraction processes to transfer solutes from one liquid to another, more infrared-transparent liquid. Each of these introduces potential complexities and inaccuracies into measurements of liquids.

One approach to address some of these limitations is to use new and improved light sources in the infrared, including quantum cascade lasers (QCLs), that offer significantly higher power at specific wavelengths of interest than traditional globar (i.e. incandescent broadband thermal emitting) sources. This higher power potentially enables absorption measurements in thicker liquid samples, while maintaining sufficient power throughput to allow reasonable signal-to-noise for measurement of chemical concentrations in the sample. Measurements can then be performed with one or more wavelengths, with one or more "signal" wavelengths at absorption peaks of interest, and possibly wavelengths designed to provide reference or baseline levels (off-peak). Multiple wavelengths may be achieved using multiple lasers, or through the use of wavelength-tunable sources.

For detection of low concentrations of compounds in liquids, or subtle changes in chemical makeup, the incremental infrared absorption corresponding to concentrations of interest may be extremely small. Therefore even with higher power transmission, there remains the problem of detecting small absorption signals against a high background.

One approach to measure low concentrations in spectroscopy is the use of reference wavelengths. For example, sample transmission at the wavelength corresponding to an absorption peak of a substance of interest is measured, together with the transmission at two nearby wavelengths, one longer and one shorter. A "baseline" is then computed using the reference wavelength transmissions, and the transmission at the "peak" wavelength is divided by this baseline. This type of baseline adjustment can compensate for factors such as sample thickness, broad absorption by other compounds, and detector responsivity changes. In the case of broadband infrared sources, it also compensates—over a limited wavelength range—for changes in source output. For example, such referencing will drastically reduce effects from changes in temperature of a conventional blackbody thermal source. Indeed, this approach allows traditional Fourier-Transform Infrared (FTIR) instruments equipped with globar sources—or even using broadband radiation from synchrotron sources—to produce spectral data that may be locally baselined (in wavelength) to accurately determine chemical content.

Such baselining techniques, however, may be significantly less effective with infrared laser sources such as those that can deliver higher power to penetrate thicker liquid samples. Laser sources are inherently narrowband, resonant devices, rather than broadband emitters. Their output—power, wavelength, bandwidth, polarization and spatial beam properties—can be highly sensitive to device and operating conditions including current, temperature, aging, and feedback (from reflections). Moreover, any changes in these conditions may cause highly discontinuous changes in output. Moreover, these changes will not be consistent from one laser to another, or even from one wavelength to another in the case of a broadband or tunable laser. As a result, changes between illumination at the "peak" (absorption, of a target compound) wavelength and "reference" wavelengths may be very large compared to the incremental absorption from compounds of interest.

One method used for gaseous spectroscopy is the use of tunable lasers that scan through an absorption peak in a short time. This is the core concept behind tunable diode laser absorption spectroscopy (TDLAS) that is already used in commercial instruments. In gaseous samples, absorption peaks are typically very narrow (<<1 cm-1) and high. This means a very narrow tuning range may be used (often <1 cm-1 in wavenumber terms) to cover reference and peak wavelengths. This tuning may be performed quickly, and with minimum variation in laser conditions.

In liquid systems, on the other hand, absorption bands become far broader, with lower peak absorptions. This requires tunable systems to cover a broader range (>10 cm-1 or even >100 cm-1, for example) which is difficult to do consistently. For example, mode transitions within the laser may occur inconsistently, leading to sharp changes in power, wavelength, and other beam characteristics at the wavelengths of interest. Similarly, multiple discrete sources operating at wavelengths over the required range may individually vary in their emission characteristics over time and operating conditions, leading to apparent changes in "reference" and "peak" transmission and errors in reported chemical concentrations.

Furthermore, although it is possible to integrate reference power detectors that monitor laser power prior to the sample, such reference approaches frequently require beam splitting optics which will introduce new optical artifacts such as fringing into the system. Thus the power split off by these optics may be different from the power delivered to the sample as a result. In addition, such a reference channel will not account for optical effects within the sample and sample chamber—which can be particularly important in a coherent, laser-based system.

SUMMARY

A system is disclosed by which coherent light sources, including QCLs, may be used to measure liquid samples, and provides significant advantages in terms of signal-to-noise ratio in measuring chemical composition of these liquids. The system may be very stable in the presence of laser and other optical train (path) and environmental changes. The system may also be used with non-coherent light sources.

The system includes an optical source and an optical detector defining a beam path of an optical beam, and a fluid flow cell disposed on the beam path defining an interrogation region in a fluid channel in the fluid flow cell in which the optical beam interacts with fluids. One or more flow-control devices are configured to conduct a particle in a fluid through the fluid channel. A motion system moves the interrogation region relative to the fluid channel in response to a motion signal, and a controller is configured and operative (1) to generate the motion signal having a time-varying characteristic, (2) to sample an output signal from the optical detector at a first interval of the motion signal during which the interrogation region contains substantially the particle and at a second interval of the motion signal during which the interrogation region contains a region substantially not containing the particle, thereby generating corresponding output signal samples, and (3) to determine from the output signal samples a measurement value indicative of an optically measured characteristic of the particle.

A microfluidic channel with laminar flow allows liquids to be presented in nearly identical configurations to the light source, in close proximity to one another, such that measurements of sample and reference fluids can be made within a short period of time during which the system remains stable. In addition, the close proximity of the fluids to one another in a common flow ensures they may be presented in nearly identical conditions (pressure, temperature, flow rate, etc.).

In some embodiments, AC-coupled detectors may be used to measure differential absorption between reference and sample liquids at one or more wavelengths as the scanning subsystem scans the beam between the liquid streams. The scan rate may be adjusted to optimize detector and system signal-to-noise ratio (SNR), for example by placing it above most 1/f noise, but still within the acceptable response range for the detector and its amplifying circuitry. Various well-known schemes for extracting and filtering a signal at a specific frequency may be used to optimize SNR. Inherently, change-sensitive ("AC") detectors such as pyroelectric detectors may be used, as may other thermal detectors such as thermopiles, or photovoltaic detectors such as cooled or uncooled InGaAs or HgCdTe detectors. Pyroelectric detectors may provide an advantage of high saturation flux (power per unit area) while remaining sensitive to small changes in infrared light as a result of differential absorption between reference and sample fluids.

Motion scanning may be achieved by scanning one or more beams optically over the microfluidic channel, or mechanically translating the sample relative to the beam(s). Many subsystems for scanning beams over samples have been produced for microscopy, and similar subsystems may be utilized in the disclosed technique.

One or more infrared lasers may be used in the disclosed technique to generate one or more wavelengths of interest, not limited to the infrared. In some cases, a single fixed-wavelength laser could be used to interrogate a specific absorption peak of a compound (i.e. analyte) that is not present in the reference liquid, but potentially present in the sample liquid. As the beam scans between reference and sample fluids, the magnitude of the change detected on the detector allows calculation of the concentration of the compound in the sample.

In other cases it may be helpful—because of interfering, non-target compounds, or because better concentration accuracy is desired—to use multiple wavelengths, including at least one "peak" wavelength (measuring an absorption peak of interest) and one or more "off-peak" wavelengths. In such a configuration, these wavelengths may be delivered simultaneously from multiple lasers (which may be in a single-chip array, or in discrete devices), or from one or more lasers that are wavelength-tunable. When multiple wavelengths are used simultaneously, these may be separated after transmission through the sample by means of thin film filters, diffraction gratings, interferometers or similar devices. Relatively broadband laser sources, such as Fabry-Perot lasers, may be used, and component wavelengths split from one another optically before detection. Alternatively, optical sources may be modulated in intensity in such a manner as to make their signals separable in the detection system.

The disclosed technique may utilize any wavelengths and lasers that result in the desired measurement capability, including but not limited to the UV, visible, near-infrared and mid-infrared regions where many compounds have characteristic absorption peaks, but also in the THz range where stronger optical sources such as QCLs are being developed.

The reference liquids used in the disclosed technique may be of several forms. In the most basic configuration, the reference liquid consists of a pure sample of the medium contained in the sample liquid—i.e. containing none of the target or analyte compound to be measured. For example, if the goal is to measure impurities (such as hydrocarbons) in water, the reference liquid may be distilled water, or a known "clean" sample of water from the site being monitored.

In other cases, the reference liquid may contain the compound of interest at a desired concentration level; for example in an industrial process where a compound is added to a liquid medium, a reference liquid mixed to exact concentration in a laboratory may be used. Therefore any signal detected as the beam in the system is scanned between sample and reference fluids indicates a deviation from the desired level. The phase, or sign, of this signal will indicate whether there is too much or too little of the compound, and magnitude will indicate the deviation level. As with many embodiments of the disclosed technique, multiple compounds may be measured in this manner at multiple wavelengths. For example, an entire "panel" could be run in continuous, real-time fashion in a brewing process—against a "golden sample" of the product. Chemometric methods as known in the art may be applied.

In another example, a medical liquid such as blood plasma may be analyzed with the disclosed technique against a standard reference that contains target levels of certain constituents, for example glucose or proteins. Any deviations may be measured with high contrast.

In other applications, the reference liquid may be a "before" sample, while the sample liquid is "after," where chemical change is monitored over time to measure degradation, for example. For instance, oil condition in machinery or electrical equipment may be monitored in this manner to track degradation and call for oil changes or other preventative maintenance. Again, the samples are presented in a laminar flow that allows nearly identical measurement conditions, and high contrast and SNR resulting from the scanning measurement. The deviations over time may be accumulated, providing both a change over a specific time period as well as a cumulative deviation over multiple such time periods.

In other embodiments, the disclosed technique may be used in a configuration where a reference fluid is split into two streams, and one stream is exposed to gaseous, liquid, or solid samples that interact with it (e.g. react with it, alter its chemical composition, or introduce external compounds into it). The result of this interaction is now the "sample" liquid, which is then measured as described above.

Examples of such interactions include compounds dissolved from the external sample into the sample liquid, including liquid-liquid extractions, gas-to-liquid extraction, and solid-to-liquid extraction. For example, such a system may enable measurement of trace amounts of a compound on the surface of a solid, by first dissolving this compound in a known liquid, and then measuring the resulting sample liquid against a pure sample of the liquid medium, with high contrast as described herein. In other embodiments, through equivalency, the inverse may be performed, that is a sample fluid is split into two streams, and one stream is exposed to gaseous, liquid, or solid media that react with it, alter its chemical composition, or extract external compounds from it. The result of this interaction is now the "reference" liquid, which is then measured as described above.

In other embodiments, the sample liquid or stream may in fact consist of the analytes or intermingled fluids formed at the interface of two liquids flowing in a laminar system, as a result of reactions between those two liquids. In this case, the interface or boundary region, or region of fluidic interaction, may be measured at various locations into the flow chamber (e.g. by moving the interrogation region relative to the fluid channel and measuring a boundary region signal from the optical detector) in the direction of fluid flow in a microfluidic channel, wherein the spatial position in the direction of fluid flow is correlated with the fluidic interaction time, and the reaction rates/concentrations or other characteristic of the boundary region are deduced from the rate of change of the infrared absorption signal from the sample stream. Thus the analyzer system and its controller may make one or more measurements of the sample or reference, or sample and reference, and the interface region, and combine at least two of those measurements to determine a characteristic of the interface region.

In other embodiments, the reference liquid may be pre-impregnated with compounds other than those being measured, in order to facilitate accurate measurement of liquid flow parameters. For example, it may be desirable to measure the exact cross-section of the sample liquid vs. reference liquid in the laminar flow channel, in order to determine sample concentrations with maximum accuracy. For this purpose, the reference liquid, sample liquid, or both may include a marker that will be missing from the other liquid or have a different concentration than the other liquid, allowing a difference to be detected by the analyzer system. This marker may not necessarily have to function in the infrared—it could be a color dye that is monitored optically in the visible range and have absorption characteristics in the infrared that do not interfere with the desired measurement.

In other embodiments, the microfluidic cell or channel may be designed to interact with the sample fluid, or be the point of injection or exposure in order to create a difference between sample and reference. The sides of the optical interrogation channel may be coated with a substance designed to create a differential reaction between sample and reference fluids, or the inlet channels to the cell may be similarly prepared. The microfluidic cell environmental conditions may be altered (e.g. through its temperature) to create or enhance a difference between sample and reference fluids. The microfluidic channel or channel sides may contain "posts", "notches" or other flow modifying structures as known in the art in order to induce desired or varying levels of turbulent flow at the sample—reference fluidic interface region and thus modify or enhance the signal in the interface region. The location of the fluidic boundary within the channel may be controlled or changed in order to change or enhance the interaction between fluids, (e.g. different locations in the channel may provide different levels of interaction due to such structures or design elements within the channel.). The analyzer may thus measure the fluidic boundary region optical characteristics at multiple points in the channel, each with a different level of fluidic mixing.

In certain applications, much of the reference liquid may be separated and re-used at the end of the laminar flow section. Sufficient reference liquid in the proximity to the sample liquid (enough to account for diffusion or other phenomenon in the interaction region between fluids) may be stripped away and discarded, with the sample liquid, and the remainder of the reference liquid being recirculated, as for example may be performed through microfluidic methods of directing different portions of the channel fluid laminar streams into different output channels of the fluidic cell as is known in the art.

In other applications, the reference liquid and the sample liquid may be allowed to fully mix after measurement by continued diffusion or by other means known in the art. The mixed fluid may then be returned to the source of the sample liquid to minimize sample loss instead of being disposed into a separate waste stream. This may be convenient in cases where the sample is highly valuable, or disposal may be undesirable due to sample toxicity, or when it is desirable to operate in a closed system. In another embodiment, the level of fluid mixing may be known and mixed fluid may be recirculated back to the fluidic cell for a repeat measurement at the mixed fluid concentration level, or forwarded to another fluidic analyzer cell for additional measurements. This may enable the fluidic measurement system to dynamically dilute the sample at known mixing ratios to obtain the optimum concentration level for the measurement, or to dilute it to a desired level that is optimal for further measurements or requirements of a downstream process. Successive dilutions and re-measurement may be used to calibrate the fluidic analyzer.

In another embodiment, the fluidic analyzer may be used as chemical specific detector for a liquid chromatograph. The reference fluid for isocratic solvent elution may be taken directly from the solvent reservoir for the chromatographic pump. For liquid chromatography systems that use gradient elution, the reference fluid is constantly changing over the course of the chromatographic run and the reference fluid for the purposes of the invention should closely match the bulk composition of the solvent. This may be done by splitting the eluate output of the liquid chromatography column and using an analyte specific filter to remove the analyte from the stream to generate the reference fluid. The reference fluid may then be measured against the unfiltered eluate in the fluidic analyzer. An example of such a filter may be a molecular sieve which would remove large molecules such a proteins.

In other embodiments, a single laminar stream of sample liquid surrounded by reference liquid (either in 2 or 3 dimensions) is required. Such a laminar flow, and the methods and fluidic devices for producing it, are well known from the fields of microfluidics and cytometry.

In still other embodiments, it may be advantageous to produce a multiplicity of laminar sample and reference streams with a multiplicity of fluid boundary regions, alternating across the flow channel. Such a configuration may allow higher SNR in the signal resulting from motion scanning, such as by changing the optical signal modulation frequency at the detector to be higher than the frequency of a controller signal that drives a repetitive motion of the interrogation region relative to the channel or fluid boundary regions.

For high transmission in the infrared, it may be desirable to use relatively thin flow channels, for example <1 mm, or in many cases <100 microns (um), <50 um, <25 um or even <10 um—depending on the transmission of the fluid, and the fluid dynamic parameters required to maintain a laminar flow.

The scanning beam and surface angles of the fluidic chamber may be arranged so as to minimize surface reflections which may interfere with measurements by variable constructive or destructive interference and even potentially feedback to the laser. As most infrared laser sources are inherently polarized, the surfaces may be oriented such that P polarized light experiences no reflection as it passes through the measurement chamber.

The disclosed technique may utilize either transmissive or transflective (where light passes through the liquid, reflects, re-passes through the liquid and then back to a detector) configuration.

The disclosed technique may incorporate surface-grazing/evanescent coupling absorption spectroscopy techniques such as the use of photonic crystals that are in contact with the sample and reference fluid flows or, more commonly, ATR prisms, where the measurement face forms one side of the fluid flow channel. In such architecture, scanning is still achieved by moving the beam (which enters the ATR, and reflects at least once off the surface in contact with the fluid) perpendicularly relative to the laminar fluid flow over the measurement face of the ATR crystal.

The disclosed technique may be used throughout the visible, infrared and terahertz range where laser sources are available. Specifically, it may be used in the near-infrared (0.75-1.4 um), short-wave infrared (1.4-3 um), mid-wavelength infrared (3-8 um), long-wavelength infrared (8-15 um), and far-infrared (20-1000 um). These are regimes where compounds have characteristic vibrational absorption lines and laser as well as detector components have been developed, capable of being used as described above.

Quantum cascade lasers (QCLs) may offer specific advantages for use in the disclosed technique. They may be fabricated to emit at wavelengths throughout the mid-infrared as well at the terahertz ranges where the disclosed technique may be used to measure liquid properties. They are available in multiple formats, including discrete narrow-band single-wavelength devices, broadband (Fabry-Perot) emitters which may optionally be combined with wavelength-selective or dispersive elements to select one or more specific wavelength bands, wavelength-tunable subsystems, and QCL arrays which may emit a number of wavelengths from a single-chip device. All of these forms of QCL may be used in the context of the disclosed technique.

Applications

Applications of the disclosed technique include, but are not limited to:

measurement of medical fluids including blood plasma, urine, or saliva against standard reference fluids for diagnostic purposes, or to monitor for controlled substances; this may include the measurement of blood glucose level;

measurement of water samples against reference water samples to test for or determine concentrations of pollutants;

measurement of biological samples against reference media to measure levels of DNA, RNA, proteins, sugars, lipids, cellular nutrients and metabolites; this includes measurement of liquids which have surrounded cells or tissue (such as cancer cells, stem cells, embryos) to measure uptake of nutrients and/or production of metabolites; measurement of DNA levels in polymerase chain reaction (PCR) tests;

measurement of large molecule biologics such as proteins, carbohydrates and lipids to determine their higher order molecular structure;

measurement of liquid samples from food, drink, or pharmacological production processes against standard reference liquids to provide feedback for production parameters, measure completion, or measure contamination;

measurement of liquids used in electrical or mechanical machinery against standard reference liquids to measure wear and schedule preventative maintenance or replacement;

measurement of airborne chemicals through trapping in a liquid stream, and comparison to a pure reference liquid;

measurement of chemical composition in solids through exposure to a liquid, and comparison of that liquid to a pure reference liquid;

measurement of the eluate fluids at the output of a liquid chromatography instrument measurement of liquids such as milk against a standard reference to determine nutritional and fat content, and other parameters; measurement of potable liquids such as olive oil against a known reference to determine authenticity and purity; measurement of potable liquids against reference liquids to measure potentially harmful impurities.

More generally, the disclosed technique may be extended to allow measurement of liquid-based samples either in flow or non-flow environments. The essential elements remain the same: and infrared laser source such as a QCL (which may operate at one or more wavelengths), may include concentration gradients (the target of this measurement system) which result in a variation in the extinction of infrared light as it interacts with the sample (where the aforementioned scanning converts this spatial variation into a temporal variation in a specific frequency range), a mechanism to guide the resulting infrared light (after scan-modulated interaction with the sample) to a detector subsystem which includes an AC-sensitive detector designed to measure changes in infrared light intensity corresponding to the scanning frequency range; the output of this detector subsystem being used to calculate concentrations of target substances in the liquid. This scanning may be performed in 1- or 2-dimensions on a liquid-based sample as described below.

For purposes of clarification, the term sample may refer to a substance to be measured in the analyzer (e.g. a fluid, a fluid with analyte(s), etc.) or when used in the context of a differential or multiple sample measurement wherein the measurements are combined to determine a fluid characteristic, sample may refer to a fluid other than a reference fluid (e.g. sample and reference fluids). The sample fluid in this instance may also be referred to as the analyte fluid or analyte sample (e.g. analyte and reference fluids).

BRIEF DESCRIPTION OF THE DRAWINGS

The foregoing and other objects, features and advantages will be apparent from the following description of particular embodiments of the invention, as illustrated in the accompanying drawings in which like reference characters refer to the same parts throughout the different views.

DETAILED DESCRIPTION

FIGS. 1A-1E are several graphs or plots showing certain illustrative optical spectra.

Figure 1A:
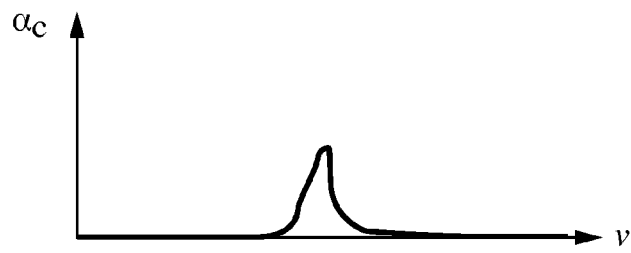
FIGS. 1A-1E are a set of plots of optical spectra.

FIG. 1A shows absorption of a target compound, in its pure form, as a function of frequency ν. In this simplified example, a single absorption peak is shown.

Figure 1B:

FIG. 1B shows the absorption of a medium in which the compound or analyte is dissolved; in this case, a uniform high absorption is shown (which is the case, for example, for water over certain infrared ranges). Note the liquid medium may have a very complex absorption profile with multiple absorption peaks, and may consist of many intermingled chemical components. The disclosed technique is very well suited to handle such scenarios where the medium has complex absorption patterns, as it inherently removes common components between a reference and sample fluid, and therefore the features of the medium in which the target compound is carried (e.g. the example where the target is in solution).

Figure 1C:
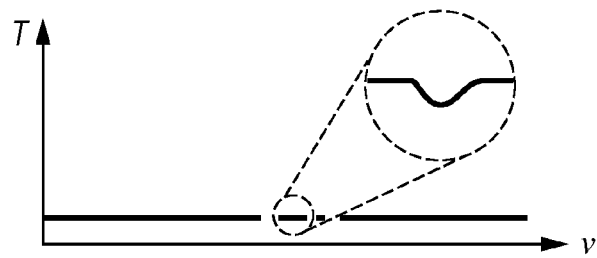

FIG. 1C shows the transmission through the liquid sample, including both the medium and target compound. Note the overall transmission may be very low (as is the case with aqueous solutions in the mid-infrared), and the incremental absorption due to the compound of interest may be extremely small. Moreover, with a broadband infrared source such as a globar or even synchrotron, the power density per unit frequency is very low, so the total power delivered to the frequency range where the compound absorbs is very low. This makes accurate measurement of samples in liquid very challenging using conventional sources.

Figure 1D:
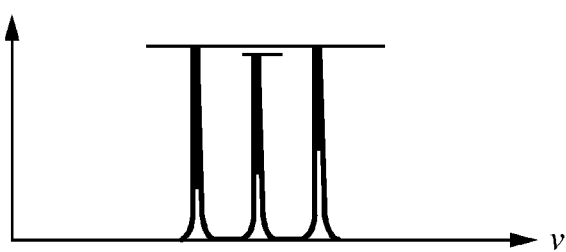

FIG. 1D shows an ideal situation in which three narrow-band infrared laser sources are used to measure reference and signal absorption frequencies, compute peak absorption, and thereby determine concentration of the compound.

Figure 1E:
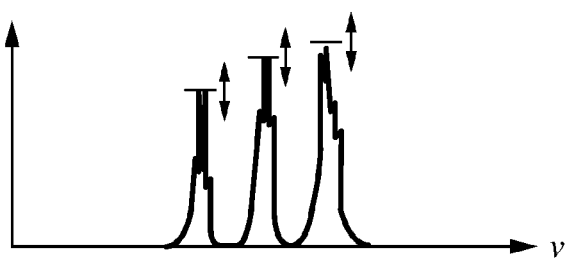

FIG. 1E shows a more realistic operation of such systems—the laser power may vary significantly over frequency, as may its bandwidths/band shapes, spatial modes, etc. These characteristics may also vary significantly with time, temperature, vibration/shock, and other environmental parameters. This means the variation in laser characteristics overwhelms differential absorption from the compound of interest in many cases, even when great lengths are taken to stabilize or calibrate the system.

Figure 2:
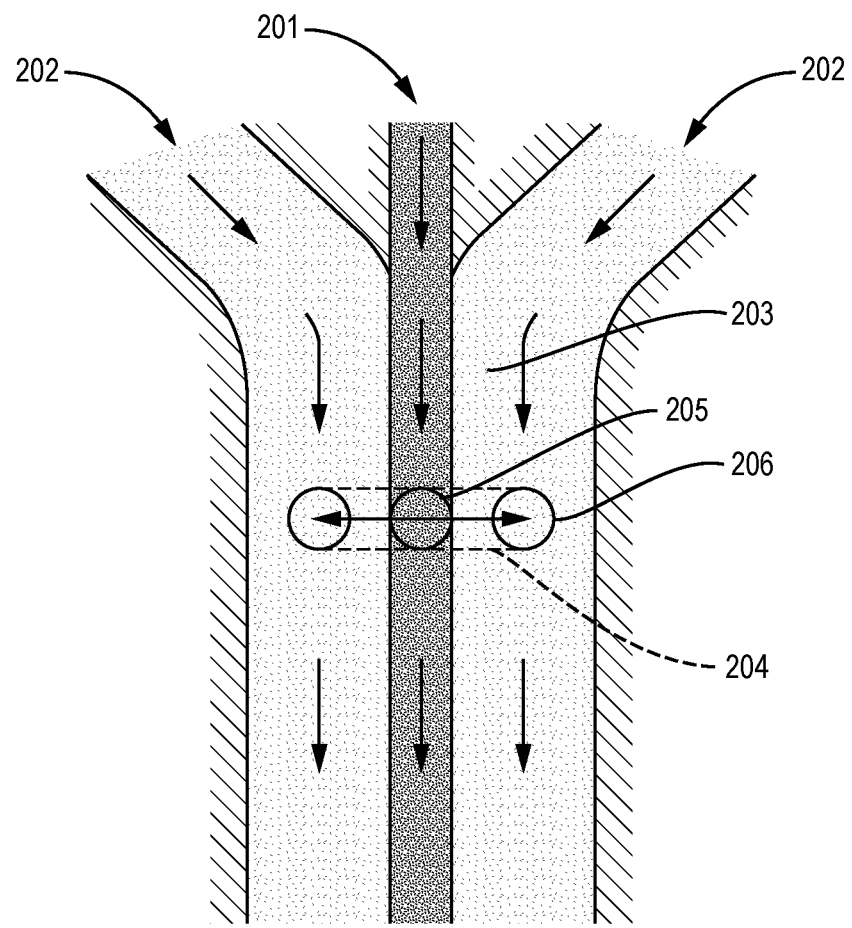
FIG. 2 is a schematic diagram of a flow channel.

FIG. 2 shows a system that overcomes such issues by presenting the liquid sample in a flow configuration that allows referencing against a standard. In this system, a sample fluid 201 flows into a chamber together with one or more reference fluids 202 with laminar flow 203. In the optical measurement region 204 a beam is scanned across the reference fluid 201 as well as sample fluid 202, with at least one region 205 where it substantially measures absorption of the sample fluid 201, and one region 206 where it substantially measures absorption in the reference fluid 202.

In the arrangement of FIG. 2, a laminar flow is established which combines the sample fluid with a reference fluid, and these flow side by side through the optical measurement interrogation zone or region within a fluidic channel. In the measurement zone, an infrared beam is relatively translated (scanned) back and forth over the reference and sample liquids. A laminar flow system, which may be a microfluidic system in many applications, ensures that there is not strong mixing between the sample and reference liquids; the parameters for such a flow (dimensions, flow rate) are well established in the art. The measurement zone may be set in a region where there is a stable flow and where significant diffusion of the compound(s) of interest between the sample and reference of measurement significance has not occurred (however, in some cases, this may be desirable, as noted above). The motion scanning range should be large enough to optically sample the sample and reference fluids adequately, but typically limited in range in order to maintain substantially identical optical path conditions in the system. In some embodiments the microfluidic channel itself may be motion translated across the beam, while in other embodiments the beam will be scanned over the channel. In other embodiments, a fluidic chamber may be pre-charged with a laminar flow, the flow terminated, and then the chamber measured optically before significant diffusion occurs. The chamber itself may be part of a disposable unit, built using low-cost microfluidic manufacturing techniques. This unit may include the reference liquid on-board, as well as in some cases any liquid required to prepare the sample fluid. Note that while the flow cell shown in FIG. 2 has two reference flows on either side of a sample flow (which is often helpful for "centering" the flow), but other configurations are possible. One embodiment would merge one sample liquid flow with a single reference liquid flow (i.e. 2 input flows), and scanning would occur proximate to the interface of these streams. More complex flows may include multiple reference and sample flows interleaved.

FIGS. 3A-3D are several graphs or plots representing the operation of the system as it is used to determine concentration of a target compound in the sample fluid, in this embodiment using a single infrared laser source and single detector.

Figure 3A:
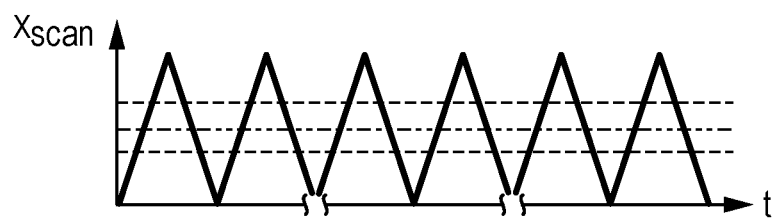
FIGS. 3A-3D are a set of plots of position, power, voltage and calculated concentration as functions of time.

FIG. 3A shows an example of a scanning pattern as may be generated from a system controller scanning modulation waveform (triangular in this case, though many other known optical scanning patterns may be used, including 2-dimensional scan patterns) where the infrared beam is scanned from reference fluid, through sample fluid, and back to reference fluid. Note that the optical beam does not necessarily need to pass across the entire width of the sample stream; it could simply oscillate on one edge of the flow between sample and reference fluids. A feedback loop may be used to continuously center the scan optimally on the edge or center of the sample flow—this feedback may use the absorption of the compound of interest, or other unrelated absorption peaks that are always present (including reference compounds added to the reference or sample liquid, as described above) as a measurement parameter in the feedback loop. The analyzer may include a transducer for detection of the position of the fluid interface (i.e. boundary region) or interfaces and generating a signal for determining the timing of the sampling of the detector output signals, such as may be performed, by way of example, with a conductivity sensor if the fluids have different conductivities, or optically if the fluids have different "colors" at visible wavelengths.

Figure 3B:
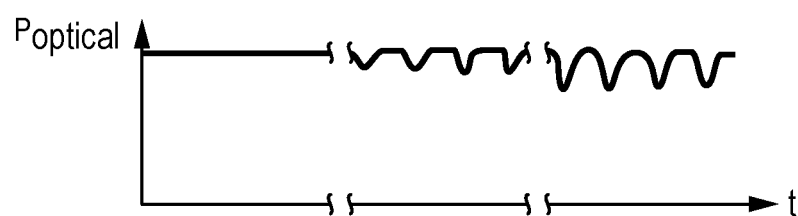

FIG. 3B shows the transmitted optical power as the beam is scanned over the channel, at three different concentration levels. The incremental absorption as the beam passes over the sample may be extremely small. Note in some embodiments, the disclosed technique may in fact be used to measure the absence or reduction of the absorption peak in the sample fluid.

Figure 3C:
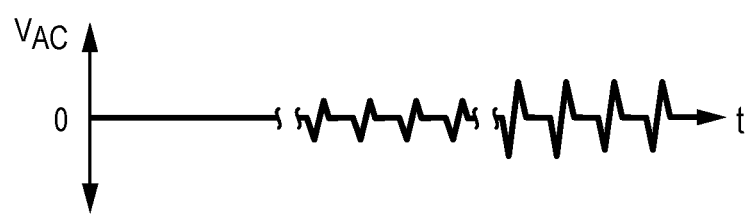

FIG. 3C shows the output of an example detector circuit in response to these optical transmission changes. The detector and/or circuit are configured in this case to use an AC detection mode, where only changes in optical power are registered (as the derivative of that power with time). Such a configuration may provide significant advantages where the incremental absorption is very small—it effectively removes the high baseline, and any common absorption features. Note that in some cases where the absorption of the target compound is high, a conventional DC detection scheme may be used. Even when an AC detection scheme is used, it may be useful to measure DC power, either with the same detector (through a split AD/DC circuit) or with a separate detector, so as to normalize the AC signal by the DC optical power (which will take into account laser power and overall liquid and system transmission, among other long-term changes). AC detectors such as pyroelectric detectors, which are low-cost and are stable over temperature, may be employed in the disclosed technique, as may the whole class of well-known detectors and circuits that have been developed for FTIR instruments (which measure AC signals resulting from a scanning interferometer).

Figure 3D:
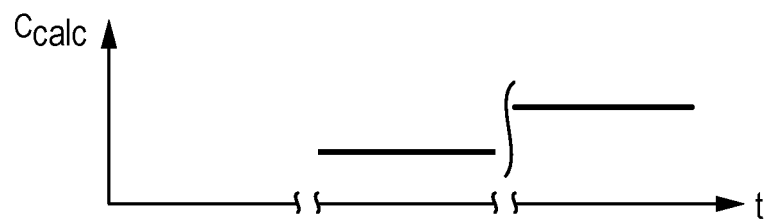

FIG. 3D shows the concentration of the target compound calculated in the current system. This concentration could be calculated from a single scan, or from the aggregate of many scans, depending on the accuracy and real-time characteristics required for the application.

Figure 4:
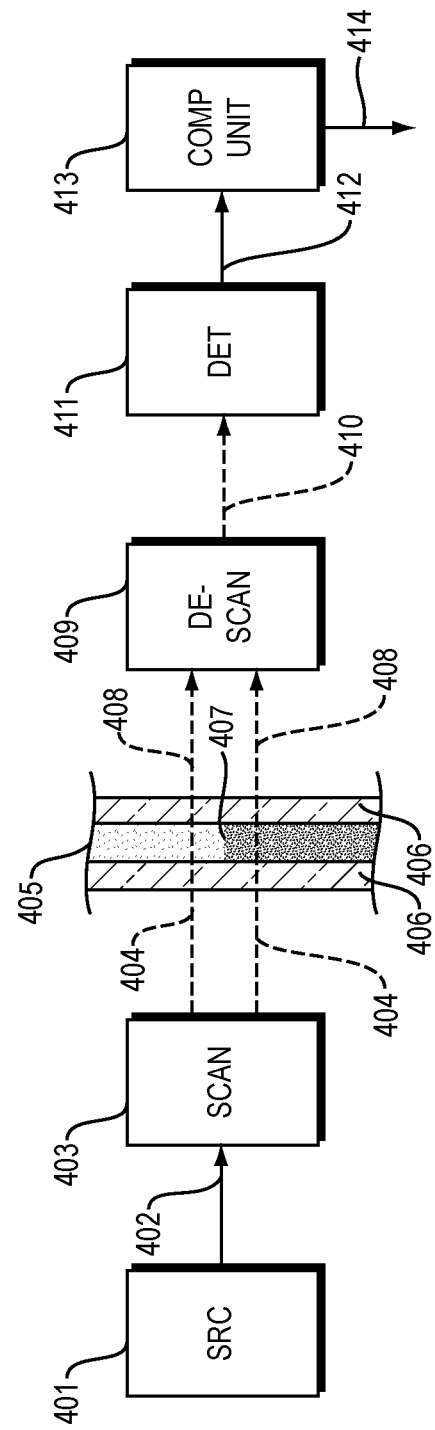
FIG. 4 is a block diagram of a fluid analyzer.

FIG. 4 presents a generalized version of the disclosed technique. A mid-infrared laser source (SRC) 401 produces mid-infrared light 402 that is motion scanned relative to a sample chamber 405 by motion control device, realized by a motion scanning system (SCAN) 403 in the illustrated embodiment. Motion scanning is also referred to as "motion modulation" herein. The scanning system 403 may be a system that translates the sample chamber in relation to a stationary optical beam. Here the scanning system 403 is shown to scan the optical beam over a range of positions 404 that pass through the chamber (e.g. microfluidic cell) windows 406 and the contained liquid sample 407 in a chamber region (e.g. microfluidic channel). As the beam is scanned through different portions of the liquid sample (the region of optical interaction of the optical beam and fluid being referred to as the interrogation region), which may contain one or more parallel streams of sample and reference fluids or combinations of both, the amount of mid-IR light transmitted at specific wavelengths may vary by transmitted beam position 408. A de-scanning mechanism (DE-SCAN) 409 serves to deliver all of this light substantially to a detector subsystem (DET) 411. The de-scanning mechanism 409 may be one and the same as the scanning mechanism 403, in the case where the sample chamber is translated to achieve the scanning, or in some cases a lens with appropriate characteristics may be used to focus substantially all the scanned light onto the detector element. The de-scanned light 410 reaching the detector subsystem 411 therefore is modulated by scanning it through the liquid sample 407, with all other conditions held substantially identical through the course of the scan. The detector subsystem 411 is an AC-coupled detector system that either uses a detector such as a pyroelectric detector which is responsive only to changes in optical power, and/or may employ a circuit to remove any DC component of the mid-infrared signal 410 reaching the detector subsystem. Therefore gain can be applied in order to amplify effects from small changes in transmission due to scanned concentration gradients, without saturating the output of the detector subsystem. The output 412 of the detector subsystem is processed by a computing unit or controller (COMP UNIT) 413 that calculates a measurement value to, in some embodiments, determine an optically measured characteristic (e.g. analyte concentration) of the fluid 414. The optically measured characteristics may be calculated as a function of position in the microfluidic channel when multiple measurement points are taken during the scanning. The controller may also generate a motion control signal for the purpose of driving the motion control device to create the motion modulation or movement.

The term measurement value as used herein generally refers to a value determined by the modulation or change of the optical power incident on the detector as a result of at least two of the sample fluid, reference fluid, fluid interface boundary region, or particle being within the interrogation region. The measurement value may then be combined with optical pathlength, optical power, or some other parameter of the analyzer to determine an optically measured characteristic of the fluids, interface region or substance within the fluids (e.g. an analyte concentration) In some embodiments of the invention, the measurement value may be the optically measured characteristic (e.g. in a biological process feedback system designed to control the signal modulation on the detector to a desired level, which may vary over time or fluid environmental conditions, the modulation signal level indicative of a target analyte concentration or other property through prior calibration of the analyzer).

In one embodiment, core elements of a disclosed system are: the use of mid-infrared lasers such as QCLs to produce light at wavelengths corresponding to compounds of interest in the liquid-based sample; a method of scanning this light relative to the sample in order to modulate transmission according to local concentrations of these compounds; a method of delivering the transmitted light to an AC-coupled detector system which amplifies these transmission differentials that result from scanning; and a system controller to compute absorption and potentially relative concentrations within the sample.

Examples of detectors types include mercury-cadmium-telluride (MCT) photoconductive or photovoltaic detectors run in AC-coupled amplification circuits, or pyroelectric detectors which are inherently AC-coupled in nature. For many applications, pyroelectric detectors may be well suited because of their AC-coupled nature, very high saturation power, temperature insensitivity, and low cost. Importantly, pyroelectric detectors remain linear over a wide range of powers (whereas MCT detectors saturate). In particular in a case where mid-infrared lasers are used, there is often plenty of power, and the disclosed technique allows concentration measurements through the detection of small changes in this power (rather than absolute DC power measurement).

The detector subsystem 411, in addition to the AC-coupled primary detector(s), may additionally comprise a DC level detector that monitors the overall transmitted mid-IR light, and is used to normalize the AC signal. Such DC-level detection allows adjustment for overall laser power, system transmission, liquid sample thickness, etc.

While many embodiments may use a transmission-type design where the scanned beam (where "scanned" is understood to mean either the beam scanning over the fluid stream, or the fluid stream being scanned (e.g. moved) relative to the optical beam) is transmitted through the sample chamber and the sample. However, the disclosed technique extends to designs employing "transflection" (where the beam passes through the sample, is reflected, and passes through the sample once more on its path to exit), as well as surface-sampling techniques such as attenuated total reflection (ATR) prism-based designs where the beam reflects off a surface in contact with the liquid sample and evanescently couples into it, evanescent waveguide designs, and designs where resonant surface coatings (such as photonic crystal or metamaterial designs) in contact with the sample amplify interaction between the mid-infrared light and the sample.

The beam scanning frequency and pattern may vary by configuration and application. In one embodiment, the scanning may allow the signal corresponding to the absorption, and therefore the concentration gradient, to be shifted to a frequency well above low-frequency noise sources (e.g. 1/f noise) and variations in the system (e.g. temperature fluctuations in the mechanics or laser, etc.) and thereby avoid many of the disadvantages of static (DC) transmission measurements systems. For example, the scanning frequency may be at least nominally 1 Hz, 10 Hz, 100 Hz, 1000 Hz, 10000 Hz or higher as the motion and detector subsystems allow. The scanning frequency may also fall into a range where the detector employed has sufficient response. For example, pyroelectric detectors are thermal detectors, and therefore have a roll-off in signal with frequency that may be pronounced over 100 Hz. The detector circuit may also be designed and optionally optimized for the scanning frequency. Well-known "lock-in amplification" techniques may be applied to isolate the signal resulting from the scanning; the phase of the detected signal relative to the scanning may be used to further refine the signal. For example, in cases where a known interface between two fluids (say, side-by-side laminar flows of a sample and reference fluid) is scanned, the change in transmitted intensity at that interface may be isolated from other scanning-related optical artifacts. Alternatively, a baseline may be established by running the scan over a section of sample known to have no concentration gradients. Various other digital filtering techniques that are well known in the art may be applied after the amplified detector signal is captured and digitized.

Figure 5:
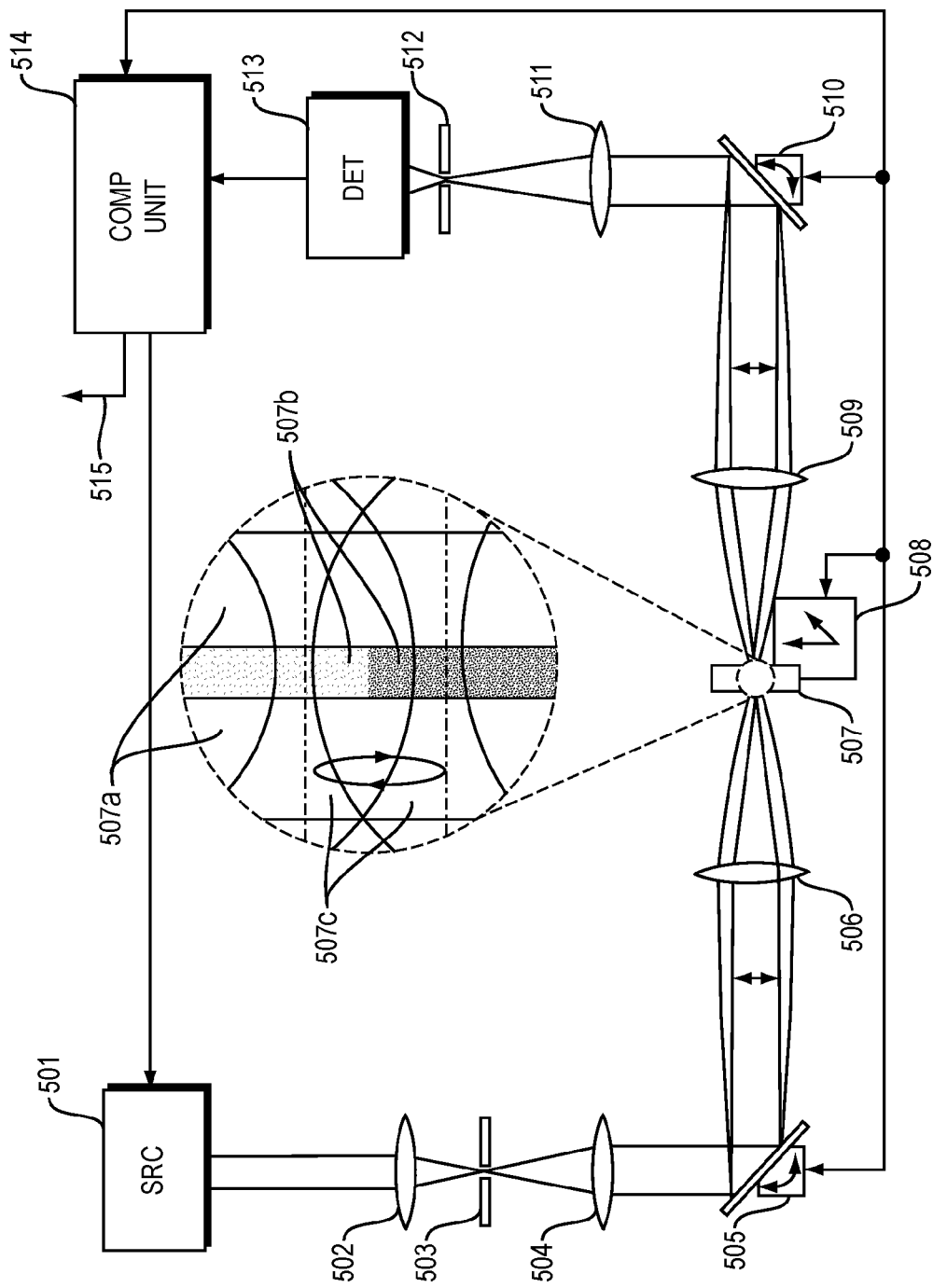
FIGS. 5-7 are block diagram of fluid analyzers.

FIG. 5 shows another embodiment of the disclosed technique. A mid-infrared laser source (SRC) 501 (which may produce one or more wavelengths in the mid-infrared) is focused by a lens 502 through a spatial filter 503 which is designed to "clean up" or optimize the mid-infrared beam, with the transmitted light well-suited for focusing into a well-defined spot (despite any variation in the output of the laser, such as different spatial modes); the filtered light is re-collimated by lens 504 and then scanned over a range of angles by scanner 505. The scanner may scan in 1 or 2 axes. The scanned light is focused by lens 506 onto sample holder 507 (e.g. microfluidic cell with fluid channel). The scanned beam 507c (showing two beam positions within the scan) passes through the sample chamber windows 507a and the contained liquid-based sample 507b (which in this embodiment, shows two regions with differing concentration of a target compound). The sample holder may optionally be mounted on a translation stage 508 with one or more translation axes in order to position the sample relative to the scanning beam. For example, a "Z" translation (substantially parallel to the axis of the beam) may be used to optimally focus the beam on the sample within the sample holder for best measurement resolution, and thereby get maximum contrast during the scan; "X" and or "Y" translation may be used to position the sample such that the scanning beam traverses specific features having concentration gradients of interest (for example, the boundary between two liquid flows). A capturing lens 509 re-collimates the transmitted mid-IR light and a de-scanning mirror 510 redirects the mid-IR light such that the light remains incident on the detector 513 with minimal intensity modulation when there is no concentration gradient in the sample. A lens 511 focuses the light, optionally through a spatial filter 512, onto the AC-coupled detector system (DET) 513. The detector signal(s) are relayed to a computing controller unit (COMP UNIT) 514 that computes absorption gradients, and potentially concentrations of analytes, in the sample. The computing controller unit 514 may also control laser operation (power and wavelength, for example), scanning and de-scanning modules, and translation stage(s), and generate scan modulation waveforms.

The disclosed technique may be used to measure liquid-based samples of various types, including liquid flows with concentration gradients, and dispersions of droplets or solid particles in liquids. Each sample will ideally have concentrations gradients over the scale scanned by the disclosed technique, so as to induce a change in the amount of light transmitted, and therefore an AC signal on the detector. The change in signal may in fact result from the displacement of the medium (for example, water) by a solute or dispersed material, or scattering as a result of the difference of refractive index between a droplet or solid particle and the surrounding medium.

In some embodiments, the disclosed technique may measure or calculate scattering resulting from particles or droplets dispersed in the liquid sample—again by scanning between regions with more and fewer of such particles or droplets, or between regions where such particles or droplets change in nature. In such embodiments, scattering may increase as a function of droplet or particle diameter or refractive index, which is a function of composition and wavelength. Through the use of appropriate spatial filters before and after the sample, it is possible to isolate or remove scattered light, and thereby calculate scattering from particles or droplets in the liquid in order to deduce average diameter (assuming some chemical composition). With multiple wavelengths around infrared absorption peaks for droplet/particle constituents, it is additionally possible to estimate both chemical composition as well as droplet size as it results from resonant Mie scattering (that is, rapid change in scattering as a result of rapid change in refractive index around a resonant absorption peak for a particular compound).

For example, in measurements of hydrocarbons in water, some hydrocarbons may not be dissolved in the water but form droplets dispersed in the water. The disclosed technique may be used to measure a sample of water with potential hydrocarbon analytes in a laminar flow side-by-side with a pure water reference, by scanning the beam (or equivalently, the sample chamber) back and forth across the interface between these parallel flows. Measurements may be made at several wavelengths, including a peak absorption wavelength for hydrocarbons, but also a non-peak wavelength. Non-peak wavelength signal may indicate scattering and water displacement; the differential between peak and non-peak may indicate hydrocarbon concentration. Additionally, if wavelengths on either edge of the absorption peak are measured, the differential in scattering loss (as a result of resonant Mie scattering) may be used to calculate dispersed hydrocarbon characteristics. Therefore the disclosed technique may be used to measure both dissolved and dispersed hydrocarbons in a water sample, and distinguish between these.

Figure 6:
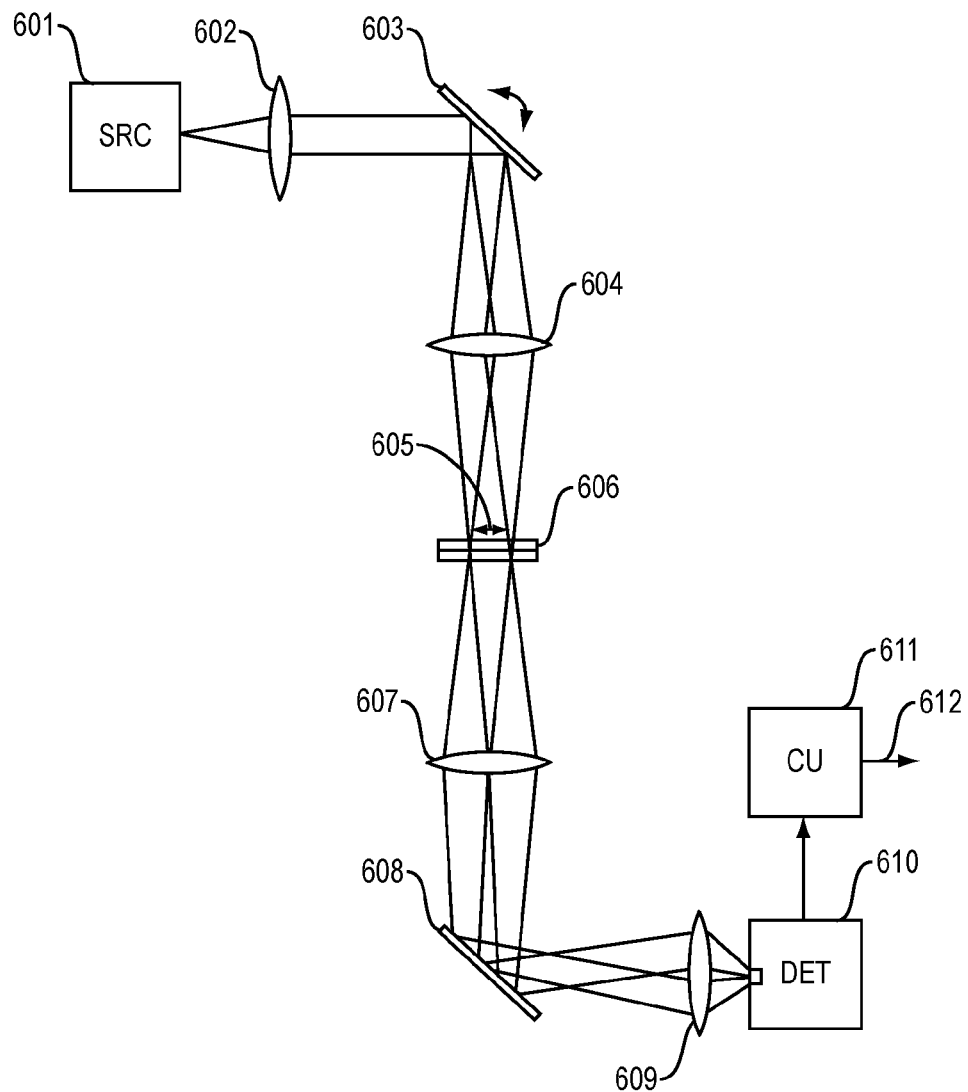

FIG. 6 shows another embodiment of the disclosed technique; this example shows a system where "de-scanning" onto a single detector element is accomplished with the use of a short focal length lens 609. A complete description is as follows: a mid-infrared laser source (SRC) 601 such as a QCL (which may be a single-wavelength device, emit multiple wavelengths, or have a tunable wavelength) is collimated through lens 602 (all lenses described herein may be refractive or reflective-type lenses), and then scanned using scanner 603 over a range of angles, before being focused on the liquid sample chamber 606 by lens 604. The sampling spot therefore is scanned over a section of the liquid sample as indicated by 605; upon transmission through the liquid sample it may be differentially attenuated depending on chemical concentrations within the sample and the interrogating wavelength(s); the beam scanning converts such gradients into a periodic power fluctuation in the transmitted light. A collimating lens 607 re-collimates the light, and in this example a fixed folding mirror 608 redirects the collimated beam to a short focal length lens 609. The function of the short focal length lens is to focus the transmitted infrared light onto the detector (DET) 610. Generally a small detector area is desired, as noise grows with the square root of area. In this example, a short focal length is used at the detector compared to the focal length of focusing lenses 604,607. As a result, the motion of the beam spot on the detector will be a fraction of the motion of the spot on the sample, allowing a reasonable scan distance on the sample while maintaining focus on the surface of a small detector. The signal from the detector subsystem may be used by a computer unit (CU) 611 to calculate absorption and possibly concentrations and other fluid characteristics, which go to output 612.

In some embodiments it may be desirable to use detectors with asymmetric dimensions (for example, an elongated rectangle), and to orient this detector with its long axis along the scan direction, to facilitate complete (or at least consistent) beam capture throughout the scan cycle. In some cases detector arrays may be used in the disclosed technique; however, the scanning would not typically result in beam spot(s) moving from detector element to detector element (which would cause very large signal swings not related to concentration gradients in the sample). In other embodiments, the optical beam with a generally elliptical spatial form may have its long axis parallel to the direction of fluid flow and its short axis parallel to the direction of motion scanning of the optical beam relative to the sample chamber.

In other embodiments, multiple beam spots may be used and scanned simultaneously across the sample. These may be multiple spots of identical wavelength, split in order to take advantage of increased performance from the use of an array of detectors (where the light from each beam remains focused on its corresponding detector element throughout the modulating scanning described herein). Alternatively, if an infrared laser array such as the distributed feedback (DFB) QCL described by Capasso et al is used, each spot may correspond to a different wavelength of interest, and may be relayed to its corresponding detector after interacting with the sample. In another embodiment, the more than one spot passing through the fluid stream may be directed to a single detector.

In one embodiment, a QCL DFB array with wavelengths corresponding to one or more absorption peaks for a target compound, plus one or more reference wavelengths to measure background absorption, can be projected onto a liquid chamber containing a laminar flow with adjacent sample liquid and reference liquids. The laser array is oriented such that the spots from the array run parallel to the flow of the liquid, and then the modulating scanning described herein scans these spots perpendicular to the fluid flow, and across any concentration gradient formed by the interface between the sample and reference fluids. After interacting with the fluid and being absorbed according to wavelength and concentration, each of these spots is relayed to a corresponding AC-coupled infrared detector (in many cases part of an array, such as a pyroelectric detector array). The modulation of each detector signal resulting from the modulating scanning corresponds to the differential absorption between reference and sample liquid at a particular wavelength; from these signals the concentration of one or more compounds within the sample liquid may be calculated.

One embodiment of "modulation" scanning (i.e. scanning that is detected by the AC detector module) may include rapid spatial scanning over small dimensions (as may for example, be used to interrogate a particle in the fluid) and slower scans over larger dimensions as may be required to interrogate the entire sample. Either scan may occur in 1 or 2 dimensions. In one embodiment, a rapid 1-dimensional scan may be used across a particular interface or feature in the fluid where there is a concentration gradient. A 2-dimensional scan may be used in a pattern to cover an area where there are concentration gradients or features on the scale of the entire sample. For example, a Lissajous-type scanning pattern may be used to relatively uniformly scan a 2D area of the sample (using simple control electronics).

Various beam or optical spot sizes and shapes may be used in the disclosed technique to interrogate the sample. These include circular spots, but also elliptical spots, the latter particularly well-suited for 1-dimensional scanning perpendicular to the long axis of the elliptical spot. For example, when scanning over the interface between two liquid flows in a flow chamber, an elliptical spot with a long axis parallel to the flow (and interface), and therefore perpendicular to the direction of scanning of the beam over the sample (or sample past beam) may provide particularly high contrast as the spot moves over the interface between liquids (compared to a more gradual change for a circular spot, for example) and may be used to detect optical characteristics of the interface. Such a configuration would be valid for transmission, transflection, or surface-sampling optical configurations such as ATR prisms integrated with the flow chamber.

Figure 7:
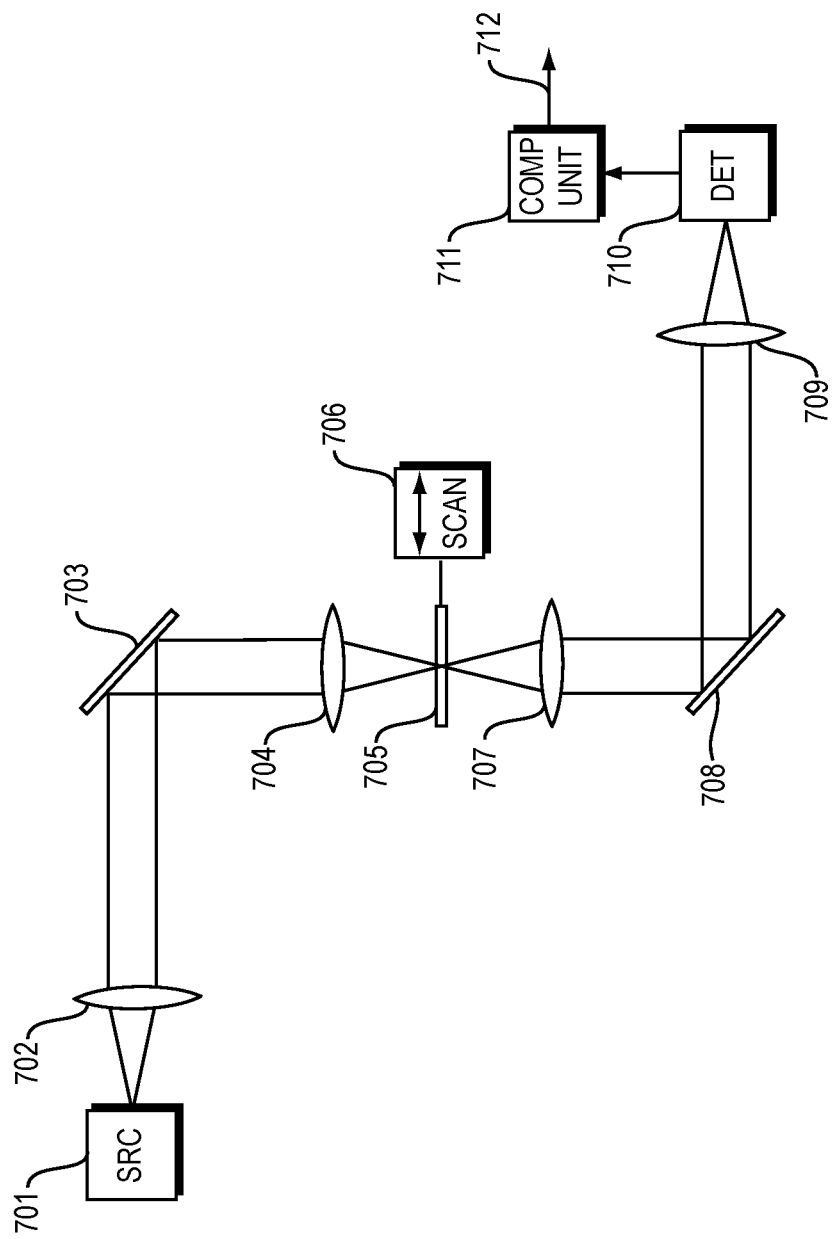

FIG. 7 shows another embodiment of the disclosed technique; in this instance the sample chamber is scanned across the beam in order to induce modulation according to gradients within the liquids. An infrared laser source (SRC) 701 is collimated using lens 702, and focused onto the sample chamber 705 using mirror 703 and lens 704. The sample is scanned using scanning subsystem (SCAN) 706, which could for example be a piezo transducer (1- or 2-axis) capable of scanning the sample at >1 Hz, >10 Hz, >100 Hz or higher frequencies to achieve the signal modulation described herein. A capturing lens 707 re-collimates the beam, which is then focused onto detector subsystem (DET) 710 by focusing lens 709. The signal from the detector subsystem may be used by a computer controller unit (COMP UNIT) 711 to calculate absorption and possibly concentrations or other optical characteristics, which go to the system output 712. This embodiment may have a drawback that the sample holder may have considerable mass and therefore require more energy to scan, and scanning may disturb the contents of the sample holder. However, an advantage is that a very consistent optical spot is maintained on the sample, reducing optical artifacts that result in non-signal modulation at the detector. In this embodiment, the sample holder may be translated both by the scanning system, as well as a secondary translation system that allows the sample to be put in focus (i.e. "Z axis" scanning), and different portions of the sample may be measured.

Figure 8:
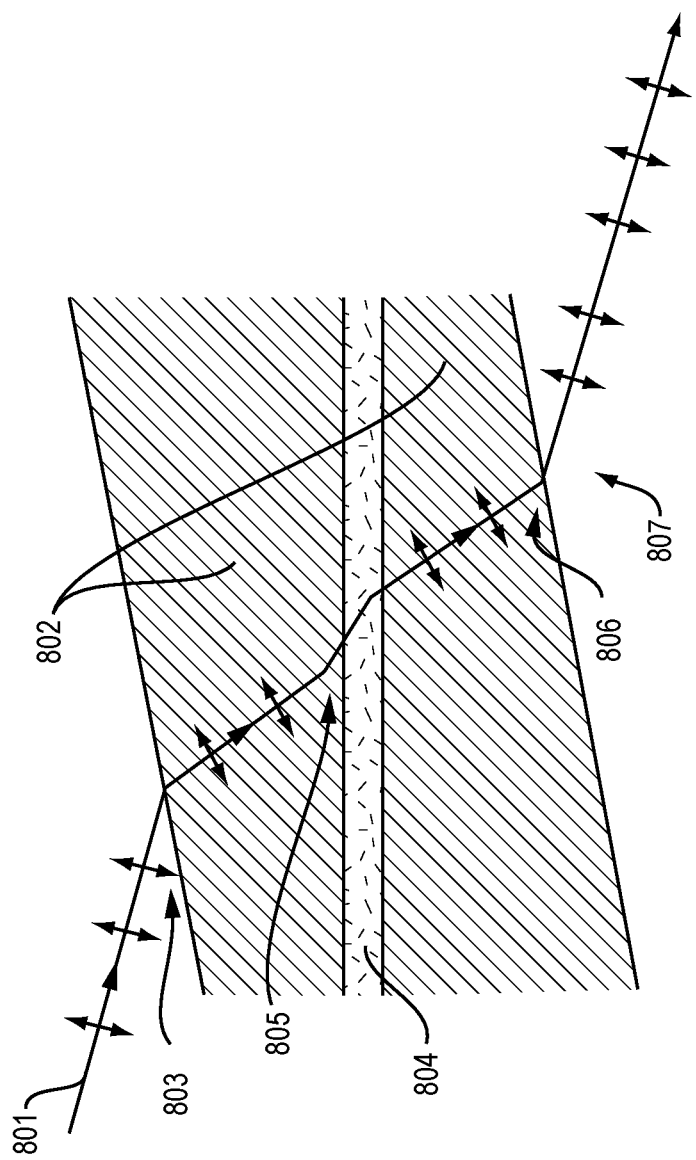
FIG. 8 is a schematic diagram of a sample holder.

FIG. 8 depicts an example sample holder for use in the disclosed technique. As light from laser sources in the mid-infrared is coherent and often has narrow bandwidth (monochromatic), issues of optical interference may become problematic. In the disclosed technique, where one or more beams is scanned relative to the sample and sample holder, small changes in reflection from the interfaces of the sample holder, compounded by coherent light effects, may cause changes in intensity of the light at the detector that are not related to the sample itself; in addition, optical interference effects within the sample holder may change the effective optical power at the sample itself (standing wave effects). Finally, reflections back to the laser source (optical feedback) may modulate the laser output (i.e. optical feedback). One embodiment may minimize changes in the optical path through the sample holder, and minimize reflections from surfaces of this holder. The example shown in FIG. 8 consists of an infrared flow cell with surface angle at the Brewster angle, or the angle where p-polarized light is transmitted without reflection through surfaces. Mid-infrared light 801 (shown here to be p-polarized) from a laser source (this is particularly true of QCLs) is highly polarized, and therefore this design may be employed without significant losses or back-reflections. The example sample holder shown in FIG. 8 consists of two infrared-transparent windows 802 which appear on either side of a liquid sample channel 804, which may contain a stationary or flowing liquid sample. The thickness of the windows 802 is for illustrative purposes only; typically the thickness of the windows will be many times the thickness of the liquid chamber or channel. The angle of incidence 803 from the surrounding medium (typically air) into sample holder window surface is at the Brewster angle, where there is no reflection of p-polarized light; subsequent angles 805 (window-to-liquid) and 806 (window-to-air) as well as the angle exiting the liquid into the window are all constructed, based on the respective refractive indices (at the operating wavelength) of the surrounding medium, window material, and liquid sample. In this manner the transmitted light 807 is free of "ghost images" resulting from internal reflections, as well as free of "fringes" resulting from resonant cavities inside the sample holder, or between the sample holder and other system components. This is of importance in the embodiment due to the modulation scanning of the beam over the sample, and therefore the sample holder. Such scanning may result in slight deviations of incident angle, as well as scanning over slight thickness variations within the sample holder windows, and other path length variations, that would be amplified if resonant cavities were to form inside the sample holder, or between the sample holder and other system components. In the present example, the beam would be scanned in and out of the plane of the paper relative to the sample holder (or, equivalently, the sample holder is scanned), so as to keep the incident angles substantially identical throughout the scan range.

Thus in one embodiment of the invention the fluid cell may comprise two optically transmissive windows defining two surfaces of the fluid channel, each window having a first surface in contact with the analyte or reference fluid and second surface, the angle of incidence of the optical beam on the first and second surfaces substantially at the Brewster angle to reduce optical reflections relative to a non-Brewster angle of incidence, and the optical beam being motion scanned in a manner to substantially maintain the Brewster angles at each sampling interval of the detectors used in determining fluid optical characteristics.

For semiconductor infrared laser sources such as QCLs, inherent spectral linewidths, or width of individual lasing modes emitted from the laser, may be extremely narrow (<0.001 cm-1). As a result of these narrow linewidths, resonant effects such as fringes may be very pronounced. For semiconductor-based laser sources in the infrared such as QCLs, it may often possible to "spread" the effective linewidth of the laser through the use of current modulation, which produces a rapid thermal modulation within the laser chip, and therefore refractive index changes that result in wavelength modulation (and concomitant amplitude modulation). In another embodiment, these lasers may be operated in pulsed mode, where their spectral linewidth may spread considerably. This is important because a broader linewidth reduces the coherence length of the emitted light—or the distance over which pronounced interference effects may occur. In traditional infrared spectroscopy applications where gases are measured, narrow linewidth is prized in order to make precise measurements of narrow gas absorption lines; however in liquid-phase samples, absorption peaks typically have peak widths on the order of 5 cm-1 or more. As a result, embodiments of the disclosed technique may include modulation or pulsing of the laser light sources in order to reduce coherent artifacts within the system. The modulation of the laser source may be done at a higher frequency than the modulating scanning described herein, and may be done beyond the bandwidth of the primary detector used in the system. Significant thermal tuning (and therefore frequency broadening) can be achieved in QCL chips, for example, with modulating frequencies of 10-100 KHz, and even 100-1000 KHz. Additionally, some QCL chips may be pulsed at high frequency, for example 10-100 KHz and even higher. At these frequencies, thermal detectors such as pyroelectric detectors do not experience a modulated signal, but a DC average of this modulated or pulsed power, and therefore the dynamic range of the detector or associated circuitry is consumed by the modulation or pulsing.

Figure 9A:
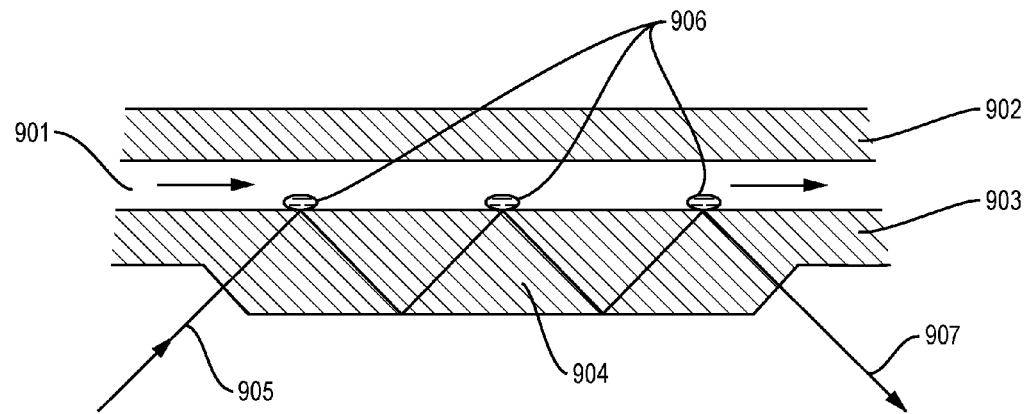
FIGS. 9A-9B show an example of a liquid chamber/channel-integrated attenuated total reflection (ATR) prism.
Figure 9B:
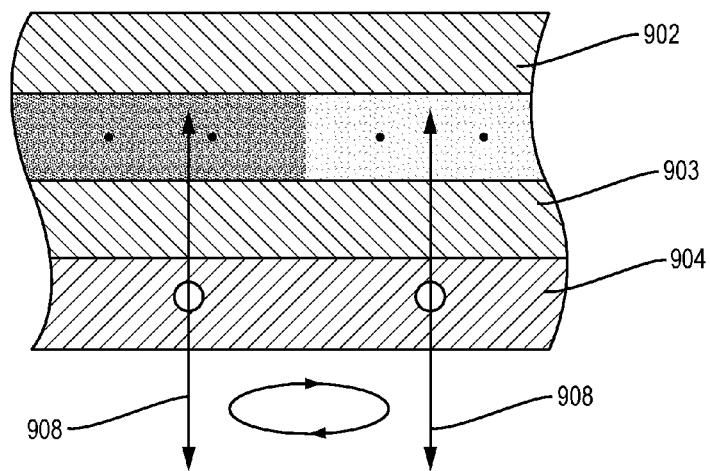

FIGS. 9A and 9B show an example of a liquid chamber/channel-integrated attenuated total reflection (ATR) prism that could be integrated into an example embodiment of the disclosed technique. This can be done to extend distances between components where back-reflections cannot be avoided to distances beyond the coherence length of the laser source(s). Such a configuration may be used in applications where the liquid medium is highly absorptive (such as water, in large ranges of the mid-infrared range), but narrow liquid channels that would allow sufficient light transmission are not feasible (because of the danger of clogging, for example). Here a liquid channel 901 carrying a flow of liquid is shown; this channel is contained between two surfaces: top surface 902 which need not be transparent in the mid-infrared; and bottom surface 903 which is constructed from an infrared-transmissive material, and has an integrated ATR prism 904. Incoming infrared light 905 enters the prism (the light and entry surface may be oriented such that the entry is at the Brewster angle, as described above), and then reflects one or more times from the surface in contact with the fluid sample. With each total internal reflection from this surface, there is some evanescent penetration 906 of the light into the channel and therefore the sample, and absorption according to the wavelength, the chemical contents of the sample and their resonant infrared peaks. The exiting light 907 is then relayed to the AC detection subsystem as described above. In this design, the beam and sample holder are scanned relative to one another in a direction perpendicular to the plane of the paper, such that the entry angle, reflection angles, and exit angles, as well as the internal distances within the prism, remain identical. The front view of FIG. 9B depicts a cross-section from the direction in which the fluid flows, with two beams 908 showing the extremes of the scan range, and the liquid showing a concentration gradient within the range of this scan that will result in a modulation signal at the detector, depending on the incident laser wavelength. This configuration may be used, for example, where a sample liquid is flowed in parallel with a reference liquid, and the scanning beam is scanned back and forth across the interface between these liquids. Any intensity modulation in the transmitted light 907, then, indicates a differential in the contents between sample and reference liquids—providing high detection sensitivity at a frequency above low-frequency noise and system drifts. The example here, again, may be used where a transmission or transflection measurement is not appropriate, because it is physically difficult to flow the sample liquid through a narrow enough channel (due to viscosity, particulates that could cause clogs, etc.)

Figure 10A:
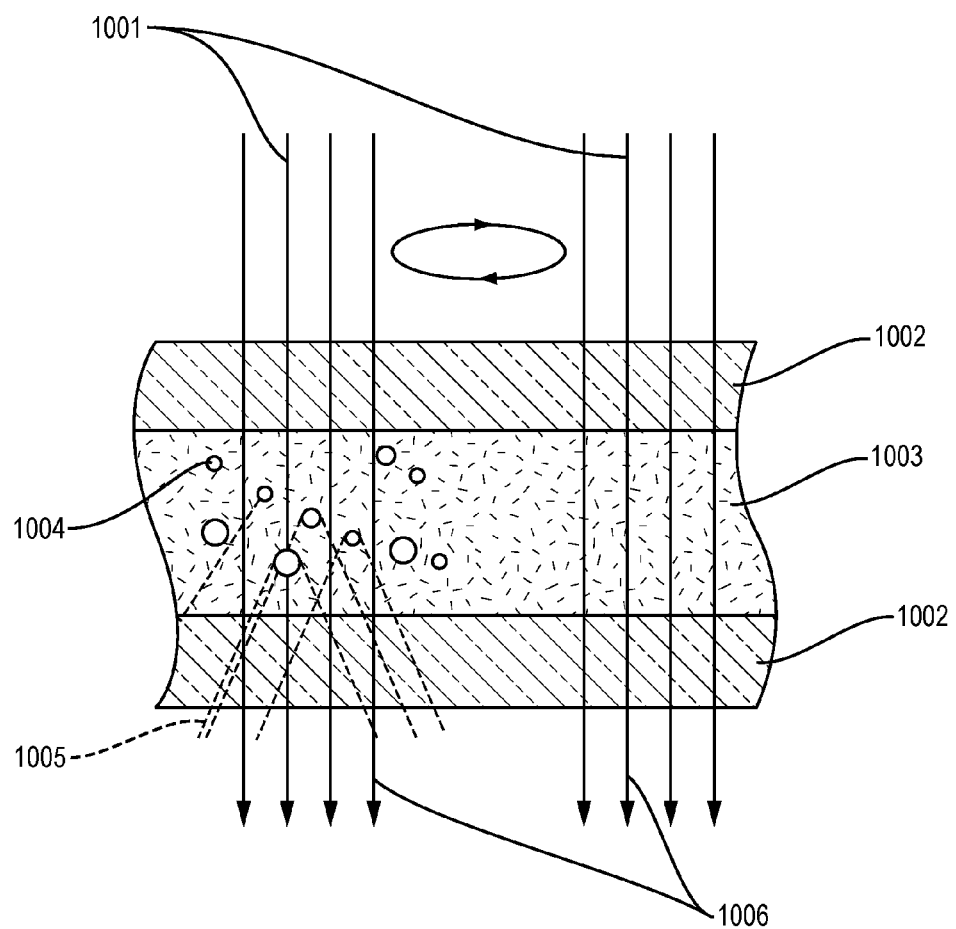
FIG. 10A illustrates a use in which a scanned liquid sample includes dispersed solids or liquids.

FIG. 10A shows an embodiment in which a scanned liquid sample includes dispersed solids or liquids—for example hydrocarbons dispersed in a water sample, or fat droplets in milk. Two incoming infrared beam positions (the extremes of a scan range) 1001 are shown as they are transmitted through a liquid sample 1003 in a channel or chamber between two infrared-transmissive windows 1002. In this embodiment, the liquid is shown to have two regions that the beam scan range straddles: one without (1003), and one with (1004) scattering particles such as suspended solids, suspended droplets, or other significant inclusions other than dissolved chemicals. The gradient in such inclusions could be a result, for example, of two liquids in a laminar flow (in or out of the plane of the page)—one of which is a sample (typically the one with the inclusions), and one of which is a reference liquid without inclusions, or with a known distribution of included particles or droplets. As the beam passes through regions with these inclusions, light 1005 is scattered as a function of the size and shape of the inclusions, as well as the complex refractive index of the inclusions relative to the liquid medium carrying them. As described above, specific infrared wavelengths may be used where particular chemical components of the inclusions (or the medium) have sharp rises or drops of refractive index (resonant regions), or high absorption. Thus, the ability to measure scattered light as a function of wavelength can allow calculation of various combinations of inclusion size, concentration, and chemical composition—or, may be used to calculate the concentration of inclusions with a particular chemical makeup (for example, resonant Mie scattering effects at specific wavelengths could be used to measure only the concentration of droplets composed of hydrocarbons, vs gas bubbles or other inclusions in a liquid).

Particle when used generally herein may mean a particulate, droplet, gas bubble, undissolved analyte or other undissolved substance with a chemical or optical characteristic different than the fluid that mostly surrounds it within the fluidic channel. A particle or concentration of multiple particles will generally have a size or sizes that result in light reflection, light scattering or measurable modulation of transmission relative to fluid without such particle or particles. Such a particle that is being transported or has been transported by the fluids, or adhering to a fluidic conduit side wall, whether in the channel, or prior to or exiting from the fluid channel, may also be considered a particle unless specified otherwise. A particle may also be an analyte.

Figure 10B:
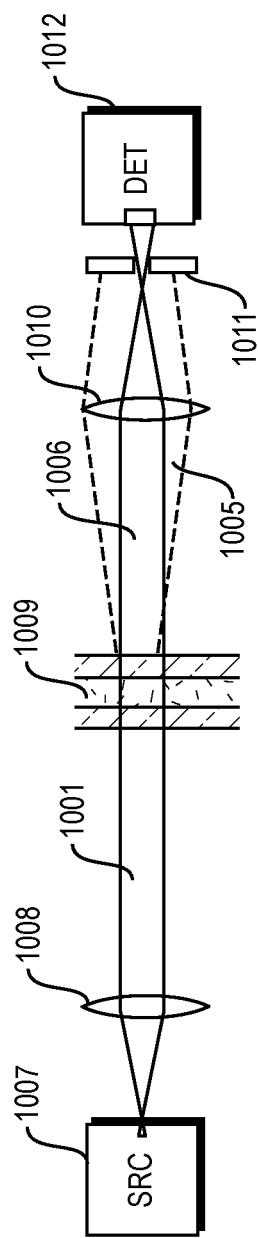
FIG. 10B is a block diagram of a fluid analyzer for a use like that of FIG. 10(a)
Figure 11A:
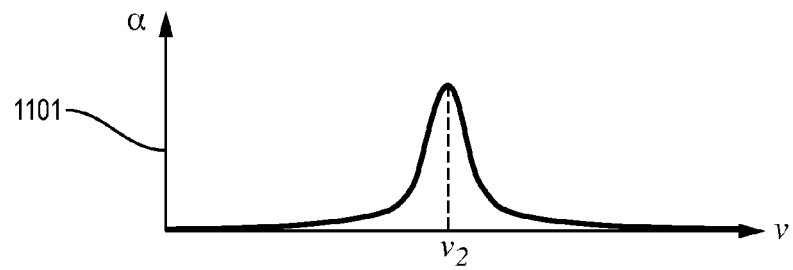
FIGS. 11A-11D are a set of plots of various parameters as a function of frequency.
Figure 11B:
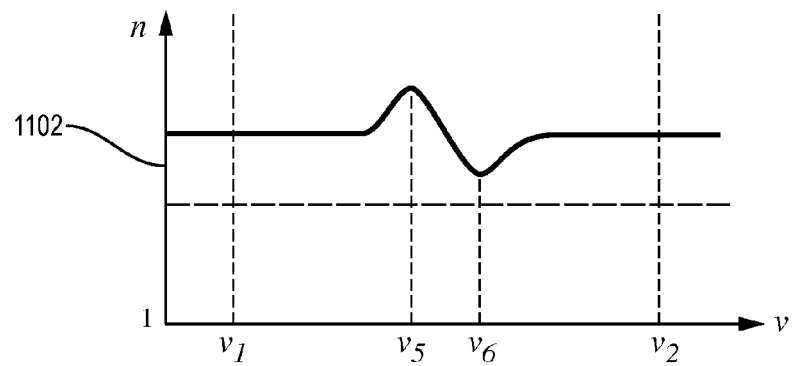
Figure 11C:
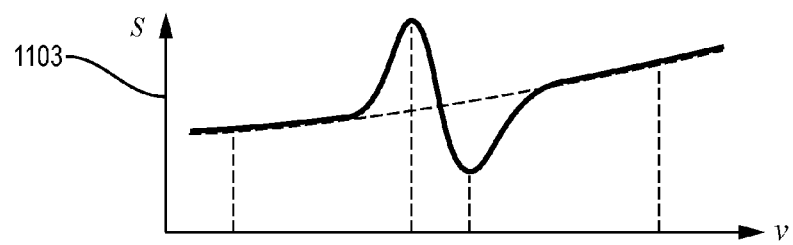
Figure 11D:
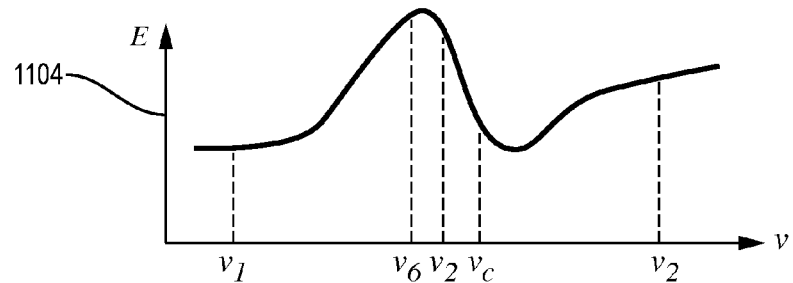

FIG. 10B shows an embodiment of the disclosed technique used to measure dispersed contents within the liquid sample of FIG. 10A. Light from an infrared laser source 1007 (which, as in all examples herein, may provide multiple wavelengths, either sequentially or simultaneously) is collimated by lens 1008 to provide a scanned beam 1001 to the liquid sample 1009. In this embodiment, scanning modulation is achieved by scanning the sample holder with the liquid sample back and forth across the beam. Some light is transmitted directly 1006, with absorption according to concentrations of species in the liquid sample and wavelength. Light that is scattered 1005 due to inclusions in the liquid emerges with a distribution of angles dependent upon the size and chemical composition of the inclusion. In this embodiment, a focusing lens 1010 is used to focus the directly-transmitted light through a pinhole aperture 1011; this aperture transmits light that passed directly through the sample with only attenuation, but preferentially blocks light that has been scattered at an angle by inclusions in the sample. The light transmitted through the pinhole aperture is then detected by a detector subsystem 1012 which is AC-coupled and designed to respond to signals at the frequency of the modulation scanning (of the sample holder past the beam). By measuring this signal as a function of wavelength, it is then possible to calculate one or more of characteristics of an analyte in the liquid, concentration of inclusions, contents of these inclusions, and/or size of the inclusions in the liquid sample.

In such scattering-measurement embodiments of the disclosed technique, it may be desirable to directly measure scattering; for example, inverting the spatial filter 1011 to block any directly-transmitted light and measure only light scattered by the sample as it is scanned across the beam. This may be repeated at several wavelengths in order to calculate one or more of total concentration of an analyte in the liquid, concentration of inclusions, contents of these inclusions, and/or size of the inclusions in the liquid sample. In other embodiments, largely directly-transmitted light may be separated from largely scattered light by use of mirrors and/or spatial filters and measured independently and simultaneously.

FIGS. 11A-11D are several graphs providing further explanation of a scattering measurement that may be employed in certain embodiments of the disclosed technique where particles, droplets or other inclusions are dispersed in the liquid sample. For each graph, the horizontal axis is optical frequency, with higher frequencies (shorter wavelengths) to the right of the graphs.

Graph 1101 shows the absorbance, as a function of wavenumber, of an example compound, with a resonant absorption peak centered at va. For standard absorption measurements, a laser source may be configured to emit infrared light corresponding to this peak, and the beam scanned over the sample containing potential gradients in concentration of this peak, resulting in a modulation of the transmitted light (as a result of the compound-specific absorption). Light at one or more other wavelengths, typically nearby to the target absorption peak, may also be used to establish a "baseline" for the peak absorption measurement (i.e. cancel out other factors and overlapping absorption signatures—not shown here).

Graph 1102 shows the real refractive index of the target compound (solid line) and liquid medium (dashed line) as a function of frequency. As a result of the Kramers-Kronig relationship between real and complex refractive index, the real index of the target compound displays a "wiggle" that is a derivative of the absorbance shown above it, in addition to a constant term. In this example, the index of the medium is relatively constant. As a result there is relatively rapid change (with frequency) of index differential between the target compound and the medium, with a local maximum at vb and a local minimum at vc.

Graph 1103 illustrates the importance of this variation in index differentials. This graph represents the scattering efficiency of a droplet or particle of the target compound resident in the medium. The scattering is a function of the size of the inclusion (held constant for the purpose of this illustration) vs the illuminating wavelength, as well as the refractive index differential. There is a general upward trend towards higher frequencies (shorter wavelengths), as the size of the particle becomes larger compared to the wavelength. Superimposed on this scattering "baseline" is the local variation due to the refractive index change around the resonant frequency of the compound (really specific molecular bond vibration modes within the compound). Where index differential is higher (νb), scattering increases, and where it is lower (νc), scattering decreases. This effect—resonant Mie scattering—occurs over a short frequency range where other factors are relatively constant.

As a result, in certain embodiments of the disclosed technique, as described above, it is possible to measure compound-specific scattering in a liquid sample. Substantially directly transmitted and scattered light may be measured separately, or the combined effects may be measured Graph 1104 is a resulting extinction curve. In this compound signal, one or more discrete frequency points may be used to measure the characteristics of the liquid with dissolved or dispersed components: frequencies ν1 and ν2 may be used to measure non-specific scattering from the sample (and therefore indicate, generally, the level of inclusions in the liquid); a laser at frequency νa may be used to assess absorption (at this frequency there is no net effect from resonant Mie scattering, but includes the baseline Mie scatter) alone when baselined using non-resonant scattering measurements from ν1 and ν2. Finally measurements at frequencies νb and νc may be used to extract the resonant Mie scattering effect, and therefore compound-specific scattering by inclusions in the system. These measurements, made using the scanning modulation system described in the disclosed technique may enable high accuracy calculation of dissolved and dispersed components within a liquid sample.

The disclosed technique is primarily focused on the mid-infrared (2-20 um) wavelength range where molecules have specific resonant absorption fingerprints; furthermore the disclosed technique may be applied in the terahertz range (100-1000 um) to which infrared laser sources have recently been extended, and where molecules likewise exhibit characteristic fingerprints. In this frequency range, it is also possible to measure interactions between molecules, or within molecules (such as proteins, when folding) using the spectroscopic techniques described herein. The disclosed technique may be used, for example, to scan the interface between two liquid samples that interact, providing high sensitivity to the resulting molecular interactions provided by the scanning-modulated liquid measurement system described herein. The laser motion in the direction of stream flow further provides for a measurement of the molecular interactions over time.

The disclosed technique comprises infrared and terahertz laser sources of all types—the key distinguishing features of such sources (as opposed to traditional incandescent or even synchrotron sources) being that: they provide relatively high power at specific wavelengths of interest; and they are coherent, small aperture sources that as a result may be efficiently collimated or focused onto a sample, and therefore provide relatively high optical power onto a limited area, which is then scanned to provide the modulation described herein. Specifically, quantum cascade lasers (QCLs) are a suitable source for many embodiments of the disclosed technique, as they can be manufactured to emit light at tailored wavelengths within the mid-infrared and terahertz bands that are the subject of the disclosed technique. Furthermore, QCL sources may be tunable (through the use of external gratings, tunable filters, or other mechanisms) over wavelength ranges suitable for measuring resonant absorptions in liquid-phase samples; furthermore, monolithically integrated arrays of QCLs with distinct wavelengths may be fabricated, again emitting over a range suitable for liquid-phase sample measurement. All of these types may be used in the disclosed technique. Other infrared laser sources, including CO2 lasers, lead-salt lasers, optical parametric oscillators, etc. may be used in the disclosed technique.

The disclosed technique may be used to measure impurities in liquids, for example hydrocarbons that may be present in water as a result of hydrocarbon exploration, exploitation or processing operations. An example embodiment for this application comprises the following:

A mid-infrared QCL source configured to emit at a frequency around a major hydrocarbon absorption band, for example 1460 cm-1. This QCL source is tunable such that it covers a range that includes the hydrocarbon absorption band, but also adjacent frequencies where hydrocarbons do not absorb as strongly (for reference levels). This QCL source may be pulsed, or modulated at high frequency (for example, 100 kHz) to spread its bandwidth and avoid some coherent artifacts in the system.

A liquid handling system that introduces the liquid sample, along with a reference liquid (pure water) into a flow chamber (e.g. a channel of a microfluidic cell) where these liquids flow in laminar fashion through a measurement cavity (e.g. an interrogation region where the fluidics interact with the radiation generated by the optical source).

One surface of this flow chamber is bordered by an infrared-transparent window, for example CaF2 or ZnSe. This window may have integrated into it an ATR prism which allows multiple internal reflections of infrared light from the surface in contact with the fluid chamber, these reflections occurring along the axis of the flow.

Optical components to relay the infrared light from the QCL source into the ATR prism, with the center position of the reflections in the ATR being close to the interface of the sample and reference liquid flows; the entry angle into the ATR and the exit angle out of the ATR configured relative to the polarization of the QCL source such that a minimum reflection occurs at these surfaces, according to the Brewster angle calculated using the index of the ATR prism material;

A sample scanning system that repetitively translates the sample holder and ATR relative to the light source incident there upon, and in a direction perpendicular to the flow and to the sequence of reflections inside the ATR. This scanning system translates the sample and the contained flow at roughly 100 Hz, for example.

Optics to capture and relay the light emerging from the ATR prism, which has evanescently interacted with the flow in the chamber, to a detector subsystem;

A detector subsystem which is configured to detect the transmitted infrared light, with electronics designed to isolate and amplify the signal that results from the scanning of the sample holder (and contained flow) and therefore the effect of the hydrocarbon concentration gradient at the border between the sample and reference liquid flows; further comprising a DC level detector which measures the average power transmitted through the system; for example, the AC detector in this system may be based on a pyroelectric detector (which is inherently AC-sensitive); the DC portion may be based on a thermopile detector; both of these are uncooled, stable, broadband and low-cost detectors;

A controller or computing system which:

tunes or switches the QCL source sequentially to wavelengths corresponding to one or more reference wavelengths (where hydrocarbon absorption is relatively weak) and peak absorption wavelength (where hydrocarbons in question have relatively strong absorption);

optionally controls the modulation scanning of the beam (i.e. interrogation region) between the sample and reference flows, within the ATR sample;

records the amplitude of modulation detected by the detector subsystem, as well as the DC power level transmitted through the system; normalizes the modulated power by the DC transmission;

calculates hydrocarbon concentration in the water by normalizing signal at peak absorption wavelength by the signal at reference wavelengths;

reports the hydrocarbon concentration in the sample;

optionally, controls the scanning or other translation mechanism to position the fluid interface (between sample and reference) at the center point of the beam vs sample holder scanning range;

optionally, occasionally positions the scanning range entirely in the reference liquid, so as to extract a baseline signal level where no concentration gradients are present;

optionally, stops all scanning motion and centers the beam on the fluid interface to observe signal from any turbulence within the flow, adjusting flow rates appropriately to achieve laminar flow and therefore a clean interface between the two fluid streams.

optionally calculates the hydrocarbon concentration using a ratio of the detector signals for a reference and sample (i.e. transmission), and the optical pathlength in the fluids The example system enables the measurement of very low levels of hydrocarbons dissolved in water samples through the use of the disclosed technique's unique infrared laser liquid-scanning plus AC detection architecture.

The method of sample introduction into the microfluidic cell may be performed in a system for online continuous measurements, or a sample fluid may be introduced into the system in "batch mode" whereby a static vessel (e.g. plunger) is filled with the sample of interest, and the sample (and reference) fluids are introduced into the cell.

When measurements of emulsions, "dirty samples", or samples that are likely to leave contaminating residue in the cell are made, it is possible to add a cleaner, which in one embodiment is optically non-interfering to the desired fluid characteristic measurement, to the reference and/or sample streams, such as a surfactant to remove hydrophobic materials such as fats or oils, or by adding an appropriate solvent. Alternatively, a cleaning solution may be periodically introduced into the cell to flush the system and clean the cell. The cleaning solution or another third reference sample may have very high, a known, or nominally 100% transmission to provide a measurement of the total laser power, thereby calibrating the prior relative amplitude measurement into a more accurate and calibrated absolute measurement.

In another embodiment, a series of measurement values are combined (e.g. co-added or averaged) to improve measurement sensitivity, and a likely presence of a particle or bubble in the fluid channel is detected through optical, pressure measurement, flow rate, fluid interface perturbation, change in the ratio of sample and reference detector output signals, or other detection methods, and samples of the detector output signal likely to have values perturbed by the particle or bubble are excluded from the series of measurement values. The particle or bubble may be detected prior to entering the interrogation region or may be detected in the interrogation region, and if detected prior to entering the interrogation region, the time the particle or bubble enters the interrogation may be projected from the fluid or particle motion (e.g. fluid velocity and distance between the detection point and the interrogation region). The bubble or particle may not enter the interrogation region and still have an effect on the dynamics of fluid motion within the interrogation region (e.g. by effecting the motion of the fluid boundary), and thus values may still be excluded. The bubble or particle may be swept along the channel or may be become lodged in the cell channel or in the fluid paths or channels entering or exiting from the cell channel, and thus still effect the measurement value and require excluded values. The relative position of the interface region between fluids and the interrogation region may be dynamically adjusted (e.g. offset from an operating position or a change in the average position during the motion modulation) during operation to account for the presence of a detector or bubble in the channel.

One embodiment may include an analyzer with chamber or microfluidic cell that (1) detects the presence of one or more analytes at a spectral wavelength where the one or more analytes have combined differential absorption relative to the solvent, and then (2) speciates between the analytes and determines their concentration in the solution at one or more other spectral wavelengths. One advantage of such a system is that it may more rapidly detect at a single wavelength the total concentration of multiple analytes or more readily detect the concentration of a single analyte in the absence of other analytes or interfering substances. In one embodiment, an analyte bearing sample fluid is measured at a single wavelength and if the analyte absorption exceeds a threshold, then the sample is held longer (i.e. literally held longer in the fluid channel or the analyzer prolongs a measurement of an analyte sample relative the case where the threshold was not exceeded) and the tunable laser is used to measure absorption at additional wavelengths in order to speciate the one or more analytes. It should be recognized that alternative combinations of wavelengths, solvent absorption and analyte absorption may be chosen for a particular application. In another embodiment, all of the analytes of interest have absorption at the selected wavelength that exceeds the solvent absorption and thus once again there is no combination of analyte concentrations (other than none) where the combined analyte absorption equals the solvent absorption.

The analyte and solvent may be immiscible liquids. It may be advantageous to ensure formation of an emulsion of the analyte in the solvent through means such as homogenization, shaking, addition of an emulsifier, or, by creating turbulent flow. The targeted particle size may be determined by the wavelength of laser light relative to the particle size. Such a particle measurement system may be used to provide feedback into the means for emulsification. Such a feedback system may also be used to change the flow rates in the cell or the absorption measurement time or both.

In various embodiments it may be advantageous to modulate the amplitude or wavelength of the laser signal synchronously with the modulation of the interrogation region position relative to the fluids in the channel. For example, the laser signal may be turned off when the transition region is transiting the beam such that system power is conserved and absorption measurements are only taken for the unmixed reference and sample streams.

Figure 12:
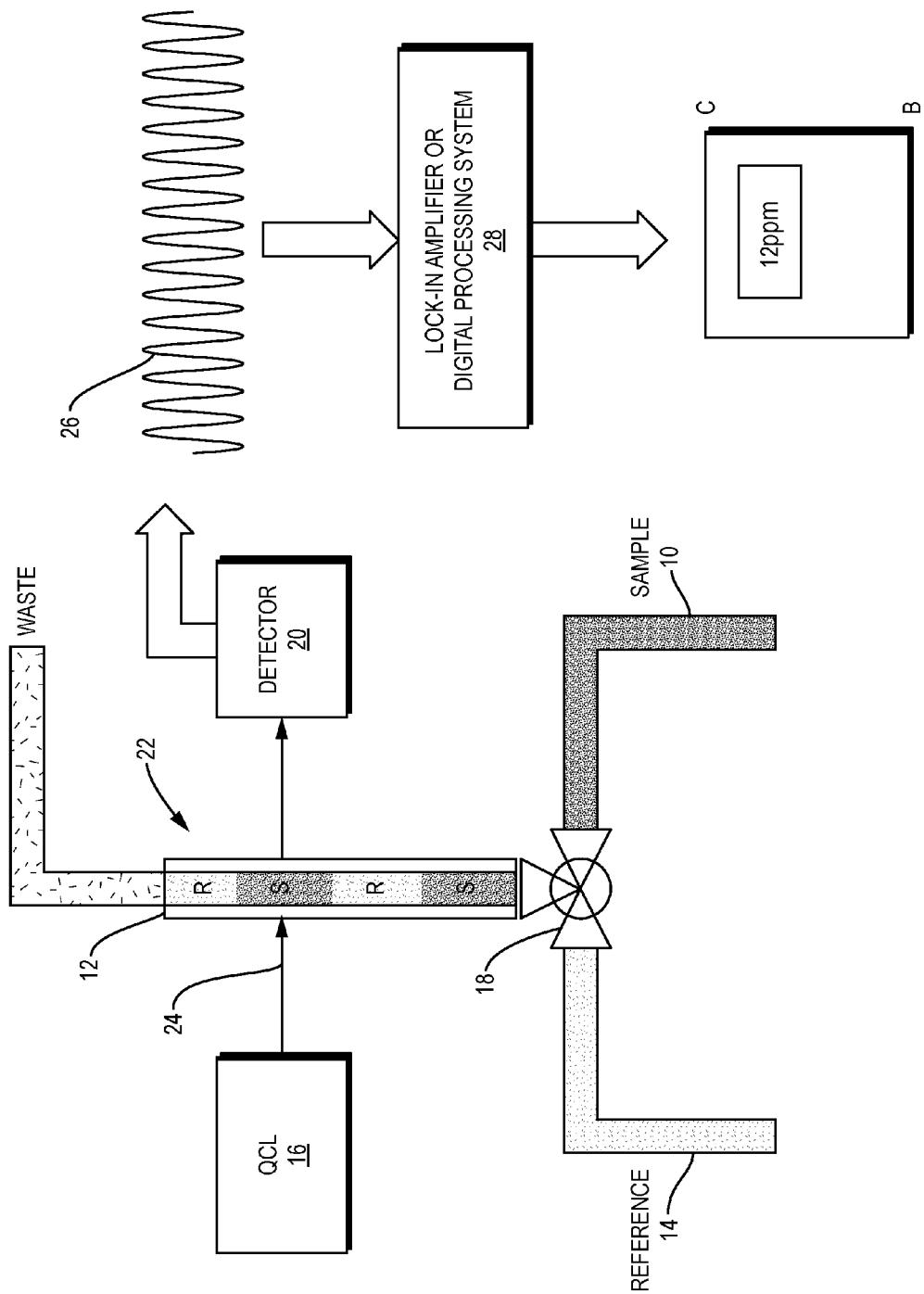
FIG. 12 is a schematic diagram of a fluid analyzer.

FIG. 12 shows a first embodiment of "serial streaming" in which a liquid sample solution 10 containing an analyte of interest is introduced into a fluid flow cell (or "flow cell") 12 in either a continuous flowing stream, or in a flow-stop-measure-start-flow repeating sequence. In the flowing stream, a reference solution 14 (the order of sample and reference can be reversed) is introduced into the flow stream in such a manner as to create alternating segments or plugs in the flow stream of sample 10 and reference 14 materials. These alternating segments are shown as S for sample and R for reference. A Mid-IR source 16, such as a fixed frequency or tunable QCL laser 16 as shown, or one or more lasers, is tuned to a suitable wavelength for measuring the analyte(s) of interest, such as the peak of an absorbance feature chosen to minimize background interferences. The Mid-IR source 16 may be coupled to the fluid flow cell 12 through a fiber. The reference material is chosen as a suitable reference material or mixture representative of the sample background as previously disclosed. The reference may be inserted into the sample stream using microfluidic techniques such as valves, mixers, or pumps (generally, flow-control devices), and/or the use of pressure to alternate the sample and reference streams, all as known in the art. In the illustrated example a switching valve 18 is employed.

Figure 13:
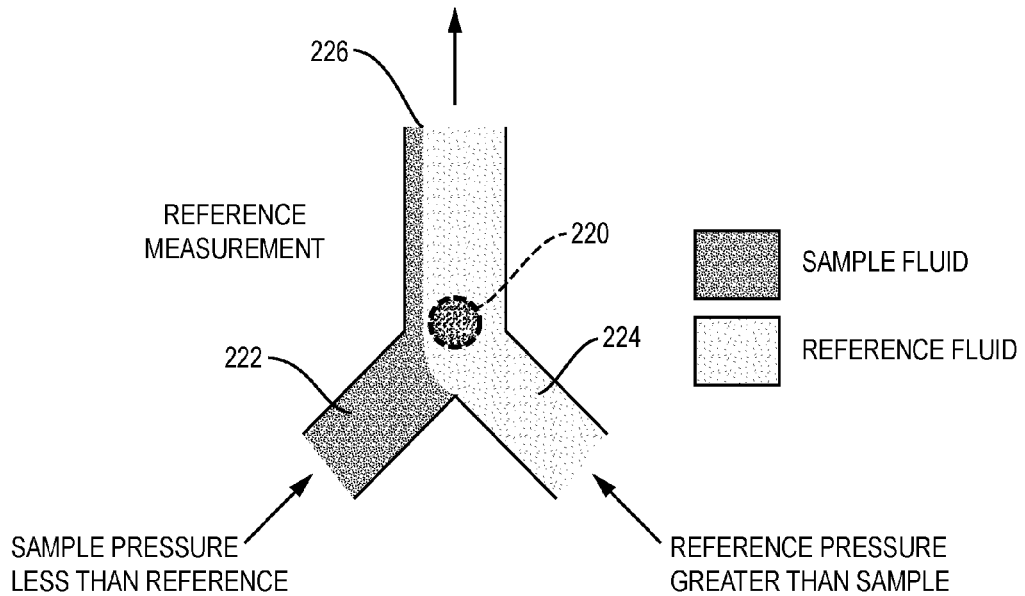
FIGS. 13 and 14 are schematic diagrams of a fluid flow cell.
Figure 14:
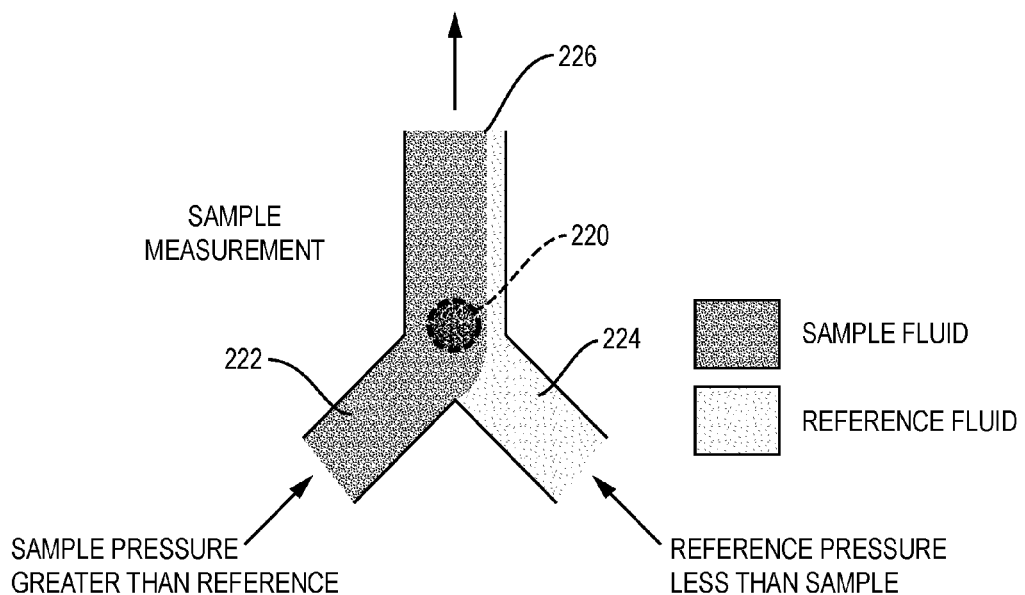

FIGS. 13 and 14 illustrate an embodiment of "parallel streaming) in which a sampling beam interrogation region 220 (i.e. the region of the flow cell channel that transmits the laser beam and is the optical absorption detection region) is placed at or near the convergence of the sample and reference streams 222, 224 in a fluid channel where they are separated by a fluid boundary or interface 226 as previously disclosed for laminar flow streams. In these Figures the laser beam is incident orthogonal to the page. By varying the relative pressure of the two streams 222, 224, the widths of the streams 222, 224 in the fluid channel 228 can be varied such that the laser beam alternatively passes through one stream 224 (FIG. 13) and then the other 222 (FIG. 14). By time varying the pressure differential between the two streams 222, 224, the frequency or rate of measurement of the sample and reference may be varied, as can the transition time when regions of both the reference 224 and sample 222 are within the interrogation region 220. The size of the interrogation region 220, which is substantially the same as the laser beam diameter, may be less than the width of the individual streams 222, 224, enabling a discrete sampling of each stream 222, 224. Alternatively, the laser beam diameter may exceed the width of the individual streams 222, 224, and multiple detectors may be used to spatially sample across the transition region or across the sample, reference and transition region streams.

Thus three general types of embodiments are contemplated for performing sample characteristic measurements as described: motion of the optical beam relative to the fluid channel, motion of the fluid in a serial streaming manner in the channel, and motion of the fluid in a parallel streaming manner in the channel. Combinations of these techniques are possible, as is the general use of laser or fluid motion in order to translate the position of interrogation point relative the microfluidic cell or fluid boundary for subsequent or simultaneous sample-reference differential measurements in accordance with the invention.

Thus, one embodiment may include:

an optical source and an optical detector defining a beam path of an optical beam;

a fluid flow cell disposed on the beam path defining an interrogation region in a fluid channel in the fluid flow cell in which the optical beam interacts with a fluid;

one or more flow-control devices configured to conduct an analyte fluid and a reference fluid stream through the fluid channel, a fluid boundary region separating the analyte and reference fluids when flowing together through the fluid channel;

a controller operative (1) to sample an output signal from a transducer to detect a particle within the fluid channel, (2) to generate a motion modulation signal having a time-varying characteristic to cause the particle to be moved relative to the interrogation region (3) to sample the output of the optical detector at one interval of the motion modulation signal during which the interrogation region contains substantially the particle and at a second interval during which the interrogation region contains substantially the fluid surrounding the particle, thereby generating corresponding output signal samples, and (3) to determine from the output signal samples a measurement value indicative of an optically measured characteristic of the particle.

The embodiment may further include a motion control device configured to position the interrogation region location in the fluid channel; an optical signal incident on the detector that has been spatially filtered for the purpose of detecting scattered optical signal, an optical signal incident on the detector that has been spatially filtered for the purpose of removing scattered optical signal; an optically measured characteristic of the particle that is an optically measured characteristic of an interaction of the particle and the surrounding fluid; an optically measured characteristic of the particle that is an optically measured characteristic of an interaction of the particle and the optical beam; or an optically measured characteristic of the particle that is an optically measured characteristic of an interaction of the particle and the microfluidic cell.

The transducer used to detect the particle in the embodiment may the optical detector or may be another transducer type. For example, the transducer may be a visible imager viewing the channel that provides an output signal to the controller indicative of the presence of the particle and its position in time in the channel.

Figure 15:
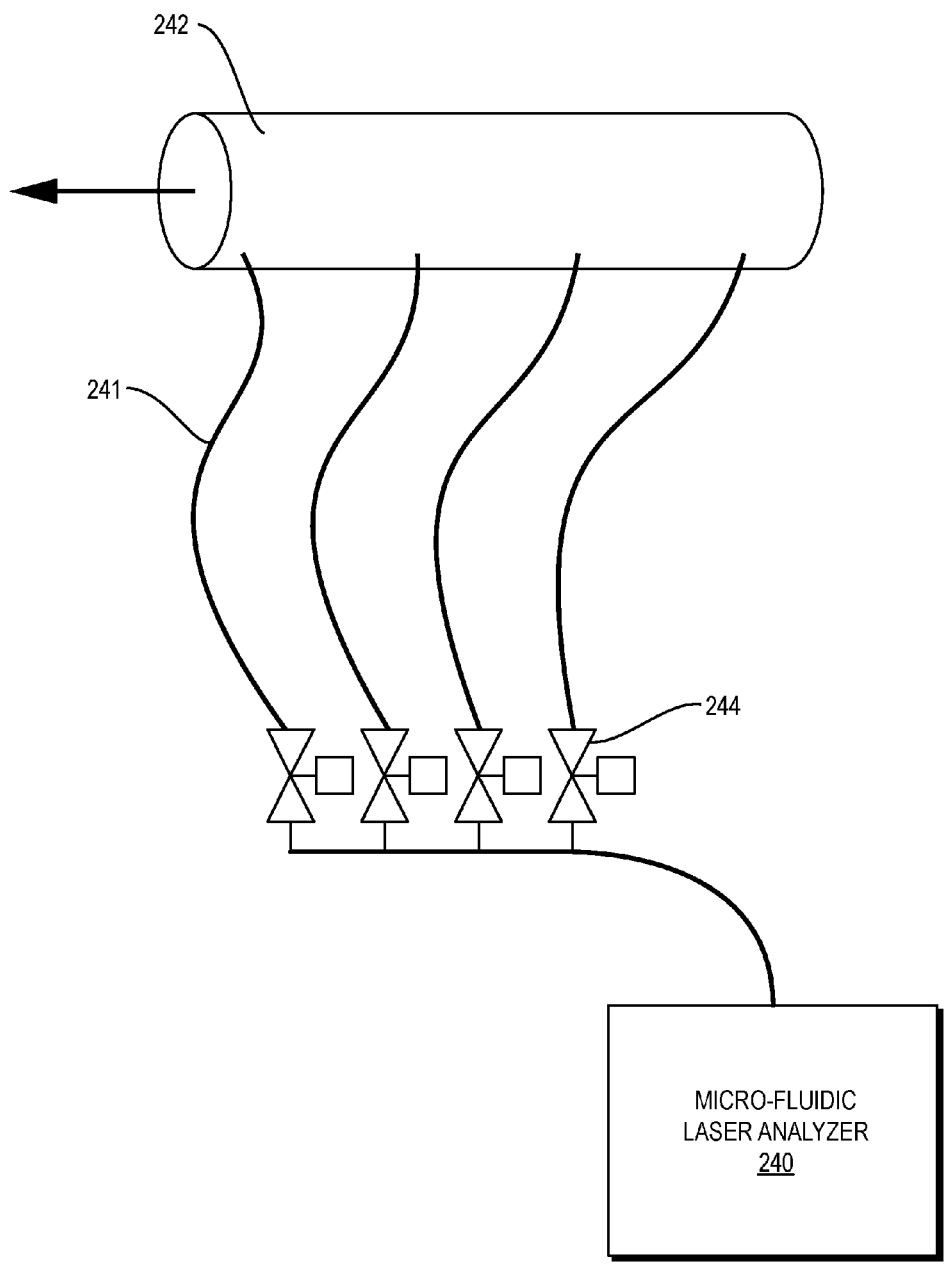
FIGS. 15 and 16 are schematic diagrams of a fluid analyzer.

FIG. 15 shows an embodiment in which the a sequence of samples are provided by sampling tubes 241 to a fluidic laser-based analyzer 240, which may be realized according to one of the above-described embodiments. In particular, the sequence is obtained by sampling a stream 242 at multiple sampling points, which may be spatially dispersed in such a manner as to ensure that the collected samples are representative of the liquid within the object being sampled (e.g. water in a pipe or container). In this manner, the small volume of the microfluidic transmission cell can efficiently sample the liquid in a larger object. Samples are sequenced by sequential operation of sampling valves 244. The spatial positioning of the sampling points may be determined by the time variant nature of the liquid in the sampled object (e.g. flowing water in a pipeline) and the timing of the absorption measurement. For example, as shown in FIG. 15, sampling points may be dispersed in the direction of water flow such that the samples are measured in the cell as if they were collected simultaneously in a plane that is perpendicular to the direction of water flow. In another embodiment, each of the sample points may feed separate sampling cells each with their own laser and detector, or sharing the same laser using beam splitting techniques well known to experts in the art. In another embodiment, each of the samples are mixed to create an "average" sample prior to being measured by absorption. In another embodiment, samples collected by each of the sampling points are sequentially passed under the measurement window permitting the separate absorption measurement of each sampling point. The separate absorption points may then be averaged in signal processing electronics. In another embodiment, the multiple samples may be combined in a high stream velocity channel that is then sampled by the flow cell at a lower stream velocity. In another embodiment, the reference fluid may be extracted from sampling stream 242 at a different location than the samples 241 and thus provide for a measurement of the change over time in flowing stream.

Sample cell or feed lines or both can be temperature controlled to bring the fluids to well controlled, constant temperature before being measured in the interrogation region. Accurate temperature control alleviates temperature dependent spectral changes (very common in polar solvents such as water, very problematic in milk measurements).

In some measurement applications it may be necessary to characterize small volumes of analyte fluids. The analyte fluid volume may on the order of the volume of the fluid channel and may even approach the volume of the interrogation region in the channel. Some embodiments of the subject invention may incorporate techniques for managing and measurement of small analyte sample volumes. An analyte sample may be inserted as a one or more fluid plugs in a serial stream that is flowed through the cell channel, each plug or plugs surrounded by reference fluid. Thus the serial stream of reference and analyte fluids volumes may not be symmetrical but may have larger plugs of reference than analyte fluids and the sample controller may generate a sampling signal when the sample fluid is in the interrogation region. The analyte sample may be directly injected into the incoming streams or cell channel using injection syringes, PZT pistons, "T" fluidic junctions, or similar approaches as known in the art, to create an analyte sample plug that is measured in the interrogation region and pushed through and out of the cell channel by the reference fluid, the analyte optical characteristics determine by the measurement of sample and reference fluids as previously disclosed. In one embodiment, the sample may be dropped into a fluidic cell channel with only three sides (i.e. with a pipette or eye dropper) and then the fourth side (e.g. a "lid") inserted to define a closed fluidic channel with inlet and outlet channels.

The insertable fourth side of the channel may be a window of the cell through which the optical beam is passed or may be a side of the channel that does not define the optical path length of the optical beam in the interrogation region.

The timing of injection and fluid flow rates, and the volume of the analyte sample, may be determined based on the rate of fluid boundary region interaction (e.g. diffusion) such that the desired analyte or boundary region optical characteristic measurement is achieved. Specifically the controller timing signals may include sampling by the detector of a stationary analyte fluid optical signal, the initiation of fluid streaming whereby the analyte sample is replaced in the interrogation region by the reference fluid, and sampling by the detector of the stationary or moving reference fluid optical signal. The reference in these embodiments for measuring small analyte sample volumes may be a gas rather than a liquid. Thus one embodiment of the subject invention may the measurement of a stationary plug of analyte sample or reference in a serial stream where the volume of the analyte sample is materially less than the volume of the reference fluid that precedes or follows it in the serial stream, and the system controller generates timing signals for sampling of the detector signal when analyte sample and reference are in the interrogation region, and for moving the fluid stream in the channel to replace the analyte sample or reference with the other in the interrogation region.

The length and relative spatial positioning of the microfluidic stream channels may be determined in part to ensure the desired temperature uniformity of the solutions being tested. The microfluidic cell may include a heater (or be mounted on a thermoelectric cooler) and temperature sensor to control the temperature of the cell and thereby the solutions flowing in the cell. The temperature sensor may be used to provide a reading of the stream temperature for use in determining fluid characteristics (e.g. absorption) by enabling an adjustment in the calculated characteristic due to temperature.

The absorption of light by many liquids has a dependence on temperature. In one embodiment, the temperature of the reference or signal liquids in the cell are changed in a controlled manner over time in order to measure an optical characteristic of the fluids or to provide a reference or calibration signal. For example, the "gain" of the system may be determined by measuring the known absorption of the reference liquid at two different reference liquid temperatures.

Variable temperature control of the cell can also be used to study the effects of temperature on chemical and biological systems. For example by incorporation of a variable temperature controlled cell one can study the conformational changes of a protein or the rate of a chemical reaction. Many chemical and biological molecules undergo rapid changes as a function of temperature. For examples, proteins undergo rapid conformational changes as a function of temperature. Due to the small volume of fluid typically passing through the microfluidic channel, it is well known that the fluid comes to rapid equilibrium with the cell. This allows for the possibility of measuring the effects of rapid temperature change by introducing the sample and reference fluids into the cell at a higher or lower temperature then the cell, and measuring the fluids at multiple spatial positions within the channel which correspond to different periods of time that the fluids have been in the cell. This could allow probing the kinetics of the chemical or biological system. Other embodiments may modulate the fluids within the channel by changing the microfluidic cell temperature or the use of discrete heaters for changing the temperature of the individual fluids separately.

In another embodiment, a laser may be used to temperature modulate the fluids prior to or simultaneous with the measurement of a fluid characteristic. The modulation may be at constant laser power (i.e. the laser increases the fluid temperature through absorption) or the laser power may be frequency modulated where the frequency may be a frequency that is less than or greater than the alternating frequency of reference and sample measurement.

Figure 16:
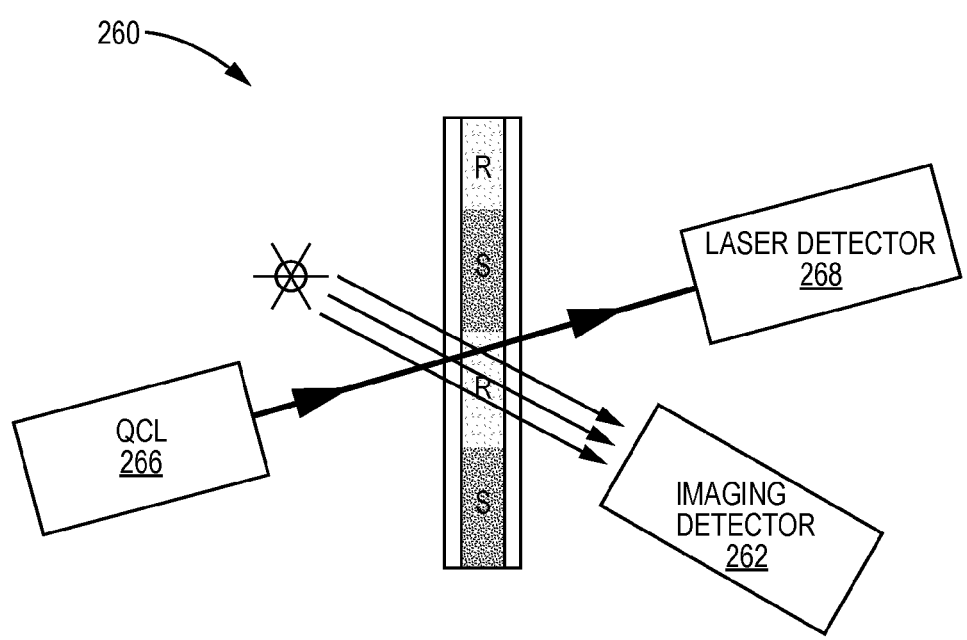

FIG. 16 illustrates an embodiment that includes an "imager" including a second source 260 and imaging detector 262 to simultaneously view the stream passing through the interrogation laser beam 264 at a second wavelength of operation. In this embodiment the sampling cell windows are substantially transmissive at both the laser and imager wavelengths. The imager may include magnification optics and use a shorter wavelength than the laser 266 (i.e. visible imager and IR laser 266). The signals from the imaging detector 262 and laser detector 268 pass to signal processing electronics (not shown), which uses the information in the imaging channel to improve the sensitivity or resolution of the absorption measurement. For example, a second channel imaging device may look for regions in the stream with particular characteristics (i.e. free of particulates or emulsions, a desired emulsion characteristics, flow rate, presence of a particle, etc.) and gate the measurement of the absorption to be inside of or outside of this region. The second channel device may be used to look for effects induced by the laser beam in the stream, such as laser induced fluorescence or thermal effects due to heating of the liquid stream. The second channel device may be used to monitor the cell channel window transmission for maintenance purposes, such as determining when the cell should be cleaned or replaced. The second channel device may be used to quantify particulates or other objects within the stream. The second channel optical signal may be enhanced by the use of an optical source such as an illuminator, LED or laser.

It may be possible to extract analyte diffusivities or other fluid boundary characteristics simultaneously during spectroscopy measurements. For example, during modulation at the analyte-reference fluid interface, the spectroscopy instrumentation is measuring analyte concentration at a fixed position along the channel (e.g. at the interrogation region) or analogously a fixed time after the fluid streams meet. Considering that the interrogation beam is modulated across the in interface, the measured analyte concentration signal over time is effectively a spatial concentration profile of the analyte. The concentration profile depends upon the diffusion coefficient, which can be ascertained directly from the concentration profile itself, given the diffusion time. The diameter of the interrogation beam may be reduced to improve measurement accuracy. For example, the beam diameter may be one tenth of the expected width of the inter-diffusion at the interrogation region. As disclosed with respect to multiple interrogation regions, the position of the interrogation region along the fluid channel (i.e. to select longer or shorter times of inter-diffusion at constant stream velocity from the point of initial stream contact) may be varied. In other embodiments, the fluid velocity may be varied to change the time of fluid interaction (e.g. inter-diffusion) prior to arrival at the interrogation region.

Thus one embodiment of the invention may include:
an optical source and an optical detector defining a beam path of an optical beam;
a fluid flow cell disposed on the beam path defining an interrogation region in a fluid channel in the fluid flow cell in which the optical beam interacts with a fluid;
an integrated temperature controller to provide constant or variable temperature control of the cell;
one or more flow-control devices configured to conduct an analyte fluid and a reference fluid stream through the fluid channel, a fluid boundary region separating the analyte and reference fluids when flowing together through the fluid channel;
a controller operative (1) to generate a motion modulation signal having a time-varying characteristic to cause the interrogation region to be moved relative to the fluid boundary accordingly, (2) to sample an output signal from the optical detector at one interval of the motion modulation signal during which the interrogation region contains more boundary region fluid than analyte and reference fluid and at a second interval during which the interrogation region contains more analyte or reference fluid than boundary region fluid, thereby generating corresponding output signal samples, and (3) to determine from the output signal samples a measurement value indicative of an optically measured characteristic of the interaction of the analyte and reference fluids.

The embodiment may further include a motion control device configured to position the interrogation region at two or more positions in the fluid channel in the direction of fluid flow where the optically measured characteristic is determined at each interrogation region position and used to determine a variation in time of the optically measured characteristic. The embodiment may further include one or more structures within the optical channel that modify the mixing of the analyte fluid and reference fluid in the fluid boundary region, and each such structure may be measured by the analyzer to determine an optical characteristic resulting from the different levels of fluidic mixing.

Bubbles, particulates, undissolved analytes and other objects in the stream may interfere with the flow of liquid in the cell. Particulates of higher density fluids may be added to the streams and the streams operated at an increased Reynolds number relative to non-cleaning operation to dislodge or remove the objects from the cell, and such particulates may be introduced as part of a special "cleaning stream" or as dispersed particles in the analyte and/or reference streams where measurements are performed between the particles. Stream velocity may be increased periodically to perform the same function. A laser optical source may also be used to heat the objects in order to dissipate, dislodge or remove the objects from the interrogation region. The laser may also be pointed or translated (or the cell translated relative the laser) in order to perform the same function at locations other than the interrogation region.

The detector may have an optical filter to pass light from the optical source and block light at other wavelengths, as for example, may be emitted through blackbody emission from objects or liquids heated by the optical source.

When objects in the streams have an optical absorption greater or less than the liquids in which they are contained, differential heating may occur. For example, an oil droplet may be heated above the temperature of the water in an oil-in-water measurement where some of the oil may be immiscible. Through blackbody emission, this differential signal may be observable when collected by an infrared point or imaging detector. The infrared detector may have an optical filter to screen out the emission from the optical source. The optical filter may also be a bandpass filter designed to pass light at specific wavelengths where the liquid has higher optical transmission. In this manner an optical source at one wavelength may be used to differentially heat an object in the liquid to create a differential optical signal between liquid and object through blackbody emission that is then collected by a filter and detector at a wavelength different than the optical source. Thus, in one embodiment both transmission and emission detection may be performed, where transmission is used to detect immiscible analytes and infrared emission is used to detect or image non-immiscible analytes. The emission measurement may be taken on one side of the cell (e.g. same side as the optical source) to minimize absorption in the liquid (i.e. shorter pathlength) with the transmission measurement taken on the opposite surface to achieve full transmission through the cell.

Figure 18:
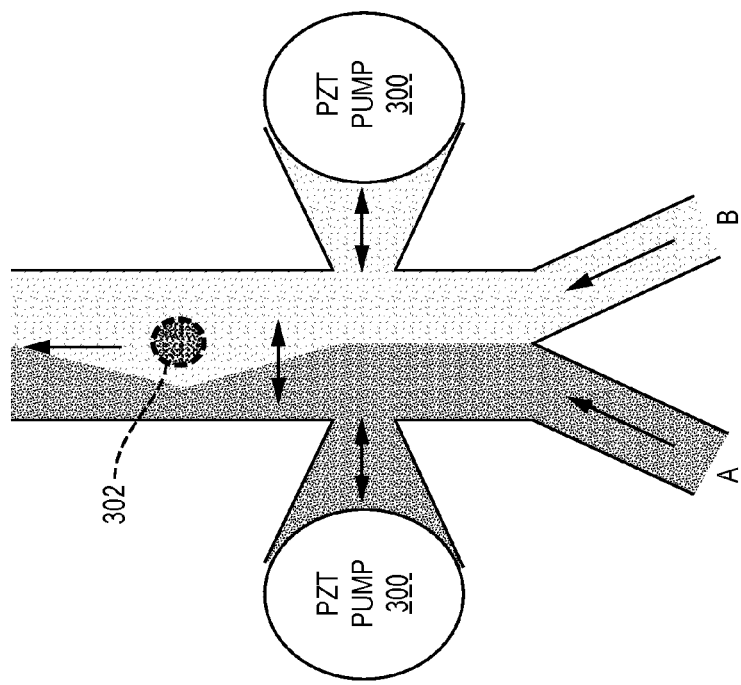
FIGS. 17-20 are schematic diagrams of fluid flow cells.
Figure 17:
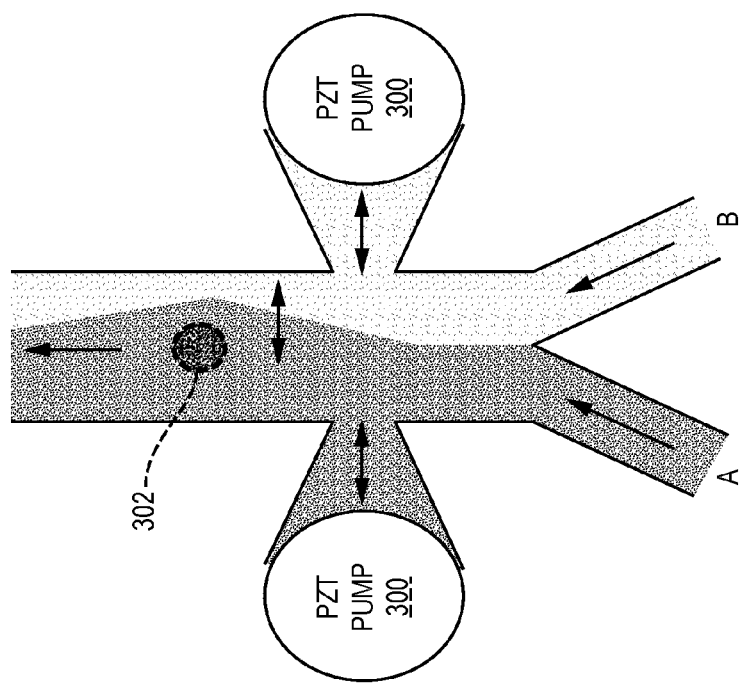

FIGS. 17-18 show an embodiment making use of one (or optionally more) PZT piston type side injection pumps 300 (or equivalent as known in the art) in the region after the two streams have merged to move the reference and analyte streams through the interrogation area. The PZT pump may be advantageous because it may not be a pump in the traditional sense of injecting liquid; it could just displace a volume in an oscillatory manner (e.g. by deforming a compliant microchannel substrate or through the use of a piezoelectric diaphragm micro-pump as known in the industry) to move the stream boundary. The use of PZT pumps and the location of the pumps may be selected to provide an increased speed of oscillation relative to modulation of the reference and analyte through the interrogation point using pressure differentials of the reference and analyte streams prior to merging (as described previously). Other types of pumps may be used. In one embodiment, the oscillations may take place at a 1 kHz rate. A lens or aperture may be used to create a smaller interrogation area. The sampling cell and fluid channel may be designed to support multiple lateral "side to side" (e.g. right to left to right in FIGS. 17-18) oscillations of the fluid boundary over the length of the fluid channel.

Figure 19:
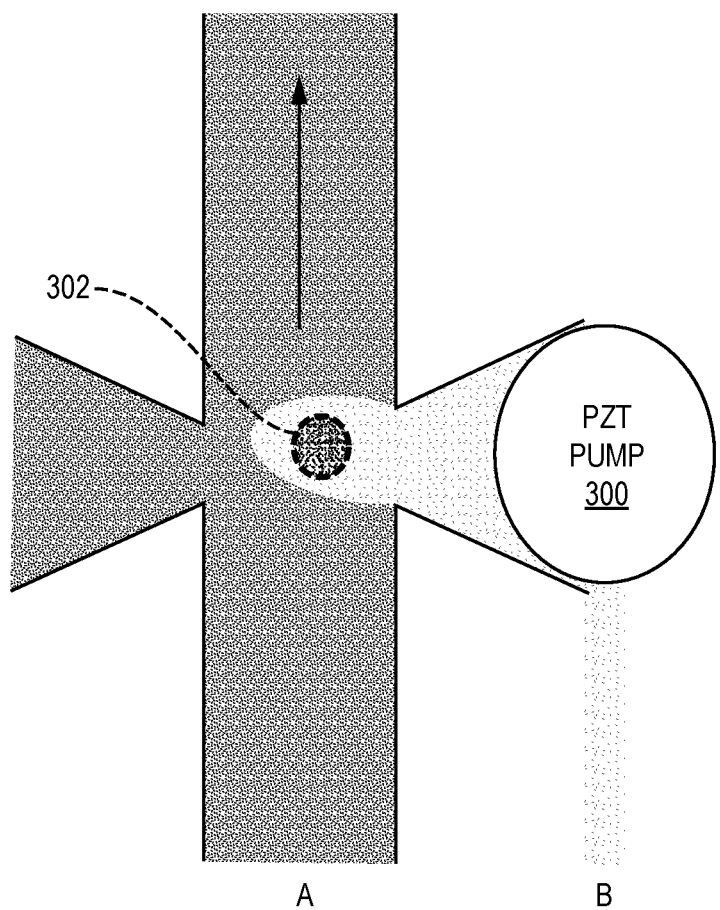

FIG. 19 shows an embodiment in which the PZT pump may be used as the injection point for the analyte B into a reference liquid A (the converse also being possible). The velocity of the reference stream A, and physical dimensions of the PZT injection orifice, the PZT pump pressure and modulation frequency may all be optimized to achieve a certain characteristic of the interrogation point, such as its physical dimensions. In one embodiment the reference liquid A may not be streaming and may be stationary for the measurement period, and then flushed to remove liquid A and analyte B. The time between flushes may be a function of the rate of diffusion of the analyte into the reference liquid. It may also be related to the viscoelastic and surface adhesion properties.

Note that as described above for other embodiments, the fluid boundary region between the reference and analyte streams may be predominately continuous in nature as in parallel-streaming, that is the boundary region is in the general direction of the stream flow, is modulated in a direction orthogonal to the direction of fluid flow (i.e. across the channel rather than along the channel) and is present in a cross section of the liquid channel (i.e. a 2-D slice taken into page as shown in FIGS. 17-18) over at least the period or time of the measurement, with the boundary region substantially or an average parallel (discounting no-slip boundaries proximate to surfaces) to the direction of fluid flow when traveling through the fluid channel. The fluid boundary region may also be discontinuous in nature (discounting no-slip boundaries proximate to surfaces), that is the boundary may be substantially or on average orthogonal to the direction of stream flow and traveling in the direction of fluid flow as may be in serial-streaming, and thus one or more boundary transitions may cross the interrogation region during the measurement or between measurements (i.e. the boundary region between fluids A and B crosses the interrogation region periodically with an orientation mostly orthogonal to the velocity vector of the fluid flow, ignoring the effect of any no-slip boundary condition). The boundary region may also be created where there is not continuous flow of liquid through the interrogation region as shown in FIG. 19 except with fluid A stationary for the period of an analyte measurement sample.

Heating of the liquid through optical absorption may result in a change in the optical transmission due to the temperature coefficient of absorptivity. If the reference streams are not identical in flow characteristics within the interrogation region, heating may result in a difference in transmission between reference and sample due solely to differential thermal heating. In one embodiment, the position of the interrogation region within the channel is adjusted to minimize (or null out) the difference in transmission. This may be a factory or field correction. In another embodiment, the differential flow characteristics may be adjusted through, for example changing the differential pressure between reference and sample to achieve the same null condition in the absence of the analyte of interest (i.e. the null is achieved for a reference versus reference condition).

In the same manner, the other stream asymmetries may be adjusted to achieve a desired null or non-zero differential transmission between reference and sample streams. For example, differences in refractive index between sample and reference may vary the effective signal collected by the detector, and the flow characteristics may be adjusted to achieve the desired differential detector signal.

In another embodiment, a heater in close proximity to one of the inlet channels may be used to differentially heat reference or sample stream. The differential heating may be used to null or reduced an optically induced differential signal in the interrogation region.

In another embodiment, the optical power may be adjusted as a function of optical wavelength. The optical power may be measured by a detector (i.e. through the use of a beam splitter to tap off part of the optical beam) and the laser operating parameters adjusted to maintain constant power as a function of optical beam wavelength in a tunable wavelength optical source. The optical power may be varied to "null" thermo-optically induced differential signals.

The channel may also be designed to have different dimensions (e.g. optical transmission pathlengths) at different locations, and thus a two dimensional moveable interrogation region may be advantageous, for example, to change the optical pathlength through the fluids. This may extend the dynamic range of the measurement to accommodate different analyte concentrations or different fluid absorption. The system controller may have a method of searching for the best interrogation region location in the channel for taking the measurement of interest that includes taking a measurement, moving the interrogation regions in the fluid channel, taking another measurement, calculating the better measurement point, and then taking a series of measurements at a preferred measurement point. The measurement of interest may be or may be related to the signal level on the detector, the measurement signal to noise ratio or the optical absorption of the reference or analyte fluids. The optical measurement point may be one that provides a ratio of reference and sample intensities equal to a desired value (e.g. 1, as for example would be the target value when reference and sample have the same absorption at the interrogation wavelength). In one embodiment, the position, size or shape of the interrogation region in the fluid channel may be adjusted in a feedback loop over more than one fluid modulation signal period (i.e. a cycle of one signal and reference measurement) to set the measured optical characteristic at a desired value for subsequent operation of the fluid analyzer. The size or shape of the interrogation region may be changed through the use of lenses or other optical elements, or by spatial movement of the fluid cell and optical source relative to each other or relative to other optical elements within the analyzer.

Figure 20:
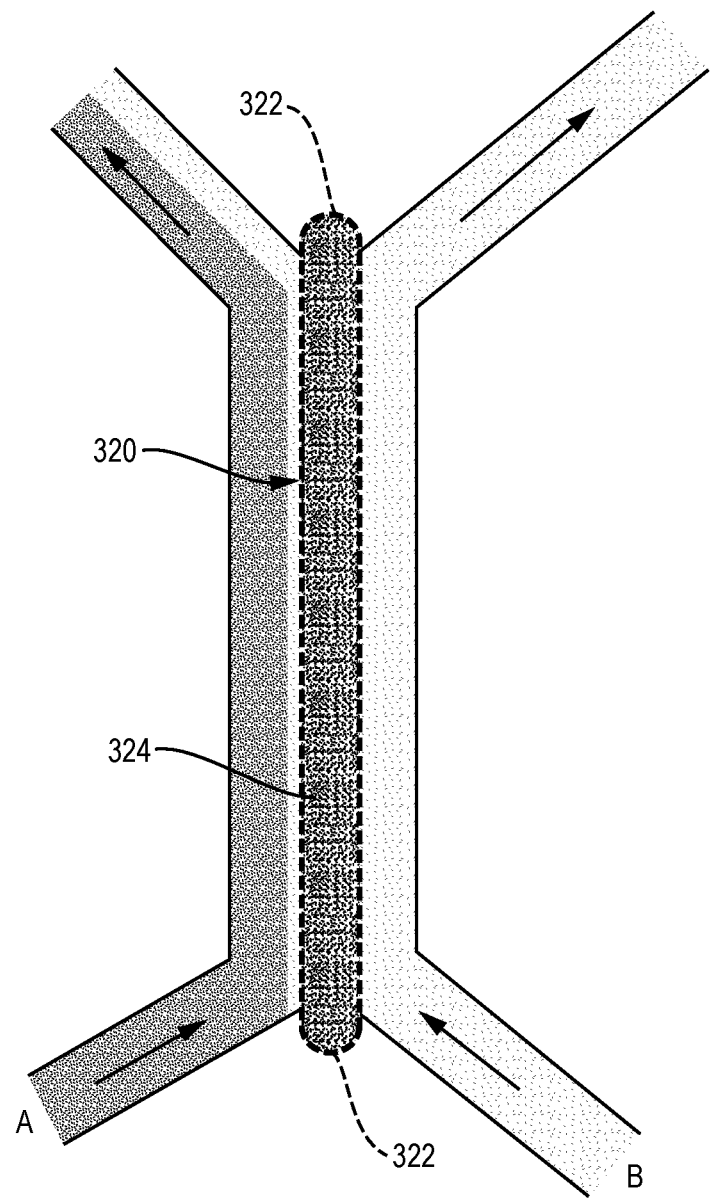

FIG. 20 illustrates an alternative configuration that can be used for increased measurement sensitivity in fluids with less absorption of the optical beam and thus may prefer increased pathlengths. The increased pathlength may be achieved by directing the moving optical beam in the direction of fluid flow down the channel 320, rather than across the channel substantially across the direction of fluid flow. The interrogation area 324 may cross a boundary region between streams A and B at one of the beam entrances or exits from the channel. Thus the interrogation area may primarily be in the middle of the channel in the direction of fluid flow to avoid sampling of no-slip regions on the channel sides and thereby improve measurement system sensitivity.

A reference solution may be used in both the reference and sample streams in order to provide a "zero" point or other calibration of the system.

In another embodiment, the reference fluid may be extracted from the same source as the sample fluid except at a different point in time, that is the reference fluid may be a time delayed version of the sample fluid (or vice versa). This embodiment may be advantageous in detecting changes in fluids or solutions over time, as may occur, by way of example, due to the introduction of contaminants, or the result of a chemical or biological process that evolves over time. The change over time may be accumulated or integrated to show not only a change over individual increments of time but the total change from the start of the process that is the accumulation or sum of the change over multiple increments (e.g. from the time the process was first sampled). The reference fluid may also be the analyte fluid with the analyte to be measured by the fluid analyzer removed by filtering, chemical processes or other means.

In one embodiment, the analyzer may be designed to operate "in situ" where the microfluidic cell is proximate or internal to the sample being measured (e.g. within a process reactor vessel), such as may be performed during the fermentation or purification processes of biologic manufacturing. During in situ operations, it may be important to ensure that the measurement itself does not have a material impact or discernable effect on the process. Thus, the analyzer may be designed to sample fluid volumes that are much less than the volume of liquid in the process reactor. The analyzer may be designed to return the sampled liquid back to the process reactor. The reference fluid may be a time delayed version of the sample fluid which may or may not be returned to the reactor vessel. The reference fluid may be an external fluid selected to not materially affect the reactor process if streamed into the vessel after measurement. The reference fluid may be filtered or chemically altered version of the analyte fluid where an analyte (e.g. protein) to be measured has been removed from, or chemically altered in, the liquid. The reference fluid may be a fluid necessary for the process reaction and thus is streamed into the process reactor following the measurement.

The presence of an analyte in the sample fluid may displace some volume of the analyte sample fluid. Since both the analyte and fluid may absorb at the interrogation wavelength(s), the signal on the detector for the analyte sample measurement may be the combined absorption of the analyte and the undisplaced fluid. If the reference fluid is the analyte sample fluid without the analyte, then a combined analyte sample and reference determination of the analyte optical characteristic in accordance with the invention may include an "offset" term resulting from the absorption characteristics of the displaced fluid, which will be different than the analyte to be measured. In one embodiment of the invention, a known optical characteristic of the reference fluid (e.g. spectral absorption) may be used to calculate a correction to a measurement of an analyte optical characteristic to account the displacement of the sample fluid by the sample analyte.

In one embodiment, the fluid analyzer may include a feedback system including a measurement system for detecting at least one spatial location of the boundary region within the fluidic channel, the location and motion of a particle within a fluid, or some other fluidic parameter or optical characteristic, a signal processor (e.g. controller) for using the detection to calculate a new operating parameter of the measurement system, and a control system for changing the operating parameter. Measurement system operating parameters or characteristics that may include: fluid velocity; fluid Reynolds number; fluid pressure; a fluid channel dimension, orifice or valve; optical beam power; optical beam or interrogation region location; interrogation region cross sectional area or volume; volume or ppm of cleaning fluid; interrogation region location in a channel; timing of the fluid modulation; timing of a transducer signal acquisition; timing of the optical beam wavelength, power or frequency variations; amount of optical beam focusing within the interrogation region; transducer location relative to the cell; choice of transducer in an array of transducers for use in calculating the analyte property of interest; selection of light source; selection of inlet or outlet channel; cell or channel temperature; power to an element for controlling the microfluidic cell or individual channel temperature; the frequency of calibration using a known input fluid or analyte property; phase of a coherent optical beam; optical fringes incident on the transducer; selection of optical pathlength in a multiple pathlength cell; interaction time or other characteristics at the fluid interfaces or particle-fluid interfaces; optical absorption of the analyte or reference fluids; phase of the fluid modulation relative to the transducer signal integration period; volume of liquid in a serial streaming packet; amount of contamination on a channel surface; amount of optical power incident on the cell that is not transmitted through the interrogation region to the transducer due to refection or other means other than analyte absorption; stroke length of a 1-D pump; motion of a flexible membrane.

In one embodiment, the analyte fluid and the reference fluid may be chosen to have substantially the same value for an optically measured characteristic and an operating condition of the fluid analyzer is adjusted in a feedback loop over more than operating condition signal period to set the measurement value at a desired level for subsequent operation of the fluid analyzer. The operating condition signal may be generated by a controller and one form of the operating condition signal may a periodic motion modulation signal used to control the fluid or interrogation region positions in the fluid channel.

In one embodiment, the effective path length may be determined with an absorption measurement of a fluid with a known analyte concentration, and the effective pathlength used in the signal processing to determine an unknown analyte concentration. The pathlength may be measured by insertion of an analyte X1 of known concentration C1 into the analyte or reference fluid and measurement of the absorption at a wavelength Y1 other than the desired absorption wavelength YU of an unknown analyte XU with unknown concentration CU. Analytes XU and X1 may have a large measured differential absorption difference at both Y1 and YU.

An analyte X2 of known concentration C2 may be inserted into a first analyte fluid for determining the effective pathlength at wavelength Y1 (e.g. at the optimal wavelength for XU), without the presence of XU (note: X2 may be XU of known concentration). The pathlength thus determined may be used in determining the pathlength in a measurement of CU. Thus, more generally, the analyte or reference fluid may contain an analyte X1 with a known value C1 for the optical characteristic, and the measured value of C1 and the actual known value of C1 are used in determining (e.g. through a calculated effective pathlength) the measured value of an analyte XU in the analyte fluid with an unknown value of the optical characteristic CU.

Thus, more generally, in one embodiment of the present invention the analyte fluid or reference fluid may contain an analyte with a known value of an optically measured characteristic, and (1) measurement value of an analyte or reference fluid optical characteristic and (2) the known value for of an optically measured characteristic are used in determining the optically measured characteristic of the analyte fluid.

In applications such as sensing oil in water, the oil (i.e. analyte) may adhere to and contaminate the optical surfaces of the cell over time. One advantage of the referencing techniques as described herein is that such static contaminate is present for both reference and sample measurement and thus can be referenced out of the measurement, as for example by the taking the ratio of the two measurements. During the measurement of the reference, a measurement of the change in reference stream transmission over time may be used to determine when window contaminate reaches a threshold value requiring cleaning or flushing of the cell interior surfaces (e.g. a detergent flush). Measurement of the change in transmission may include measurement of the emitted laser power through the use of an independent laser power measuring detector. Measurement of the change in transmission may include measurement of the absorption when both reference and sample are the same fluid. Measurement of multiple wavelengths with a tunable laser may also be used to determine the level of cell contamination, type of specific contaminating analyte or both.

Described herein is a method of measuring an analyte (e.g. oil or contaminant) in a liquid with one or more of the following:
1. Creating adjacent spatial regions of a reference liquid and an analyte liquid (e.g. water reference and oil-in-water as analyte liquid, the reference and liquid being the same fluids except for the presence of the oil)
2. Illuminating an interrogation region with a light source at one or more optical wavelengths (e.g. a wavelength of infrared laser light)
3. Moving the interrogation region between the reference and analyte liquids such that the interrogation region contains predominately the reference liquid and then the analyte liquid
4. Measuring a resultant time varying interrogation signal with a transducer (e.g. an infrared detector measuring modulated transmitted or reflected light)
5. Using control electronics to process the time varying transducer signal over one or more cycles of the interrogation signal to calculate a desired analyte optical characteristic (e.g. the amount in ppm of the analyte oil in the analyte liquid water as a form of spectroscopy)

The method may additionally be including one or more of the following:
1. Modulating the interrogation light source to improve analyte detection sensitivity
2. Adding multiple interrogation regions, each with their own illumination source at a different spectral wavelength or different transducer for measuring physical properties
3. Adding multiple interrogation regions, each with the same illumination source
4. Measuring the optical thickness of the reference liquid or analyte liquid at the interrogation region
   a. Using signal processing, simultaneously or sequentially, to correct the analyte property being measured to account for variations in optical thickness of the reference liquid, the analyte liquid or both.
5. Moving the boundary region between fluids by varying the pressure of the reference liquid, analyte liquid or both
   a. Generating the pressure variation through the use of a valve or a pump or both where the boundary region moves simultaneously or synchronously or both with the pressure variation at the pump or valve.
6. Modulating the light source in intensity or wavelength (or both), and using that modulation signal from the electronics to improve the accuracy of measurement of the analyte property.

Overall, the disclosed technique may employ four types of motion:
1) Laser motion scanning of the laser beam (and therefor the interrogation region) relative to the fluid channel and while performing a sampling of sample, reference or interface region as part of a measurement that combines at least two of the measurements to determine a characteristic of the fluid.
2) Fluidic motion scanning of the fluids (and fluidic interface region) at an interrogation point that is fixed relative to the channel while performing a sampling of sample, reference or interface region as part of a measurement that combines at least two of the measurements to determine a characteristic of the fluid.
3) Laser motion translation of the laser beam relative to the fluid channel in order to determine a location in the channel for motion scanning of the laser beam or fluids.
4) Fluidic motion translation of the fluids and fluidic boundary in order to determine a location in the channel for motion scanning of the laser beam or fluids.

The embodiments as disclosed herein may use one or more of these types of motion. For example, a particulate in the channel may be laser motion scanned by moving the interrogation region with respect to a particle, or may be fluidic motion scanned by moving the fluid and therefor a particle contained therein with respect to a fixed interrogation region in the channel. Similarly, a particle traveling down the channel in a fluid stream may be fluid motion scanned while the interrogation region is translated down the channel through laser motion translation.

In one embodiment, laser and fluidic motion scanning and translation may be performed simultaneously. The timing of a first motion waveform (e.g. a sinusoidal signal) that determines the laser motion (the laser or interrogation region motion or motion modulation waveform) and a second motion waveform (the fluidic motion or motion modulation waveform) that determines the fluidic motion may be synchronous or asynchronous with respect to each other. The various translation and scanning laser and fluidic waveforms may be correlated or superimposed with respect to each other, and the actual spatial motions of the laser and the fluidic boundary thus may be correlated with respect to each, correlation implying that the waveforms or motions are not independent of each other. For example, one or more of the following operating scenarios may performed by an analyzer system:

Synchronous and out of phase laser motion scanning and parallel streaming fluidic motion scanning such that the effective velocity of the interrogation region with respect to the fluid is increased over the effective velocity for either laser motion scanning or fluidic motion scanning alone (e.g. the optical beam is moved in the opposite direction to the direction of motion of the parallel streaming fluid boundary during the sampling of the streams). The fluidic motion and the interrogation region motion waveforms may be at the same frequency or an integer multiple of frequencies with respect to each other.

Synchronous and in phase laser motion scanning and parallel streaming fluidic motion scanning such that the effective velocity of the optical beam and interrogation region with respect to the fluid is decreased over the effective velocity for either laser motion scanning or fluidic motion scanning alone (e.g. the optical beam is moved in the same direction as the direction of motion of the parallel streaming fluid boundary during the sampling of the streams).

Synchronous and in phase laser motion scanning and parallel streaming fluidic motion scanning such that the optical beam moves in the same direction as the motion of the parallel streaming fluid boundary (e.g. the analyzer takes one or more consecutive samples of only the reference fluid, sample fluid or fluid interface region over one or more cycles of a motion waveform as may happen when the interrogation region motion is the same as the fluid motion and thus the interrogation region is stationary relative to the fluid interface boundary region). This may be advantageous, for example, to sample the fluids or interface region at different locations in the fluidic channel as part sample measurement or calibration of the analyzer, all without performing a ratioing or differencing of sample and reference streams.

The fluid interface boundary region may be moved back and forth across the fluidic channel and the laser beam may be motioned controlled such that it continuously samples the sample, interface (optionally) and reference fluidic regions at a motion waveform frequency higher than the motion waveform frequency of the parallel streaming fluidic motion translation. In this manner, the differential measurement samples are taken at multiple locations in the channel during laser beam motion scanning. The frequency of the motion modulation may be an integer multiple of the fluidic streaming modulation such that an integer number of laser motion scanning reference and sample measurements are taken for each cycle of the parallel streaming boundary translation waveform.

As the fluid interface boundary in serial streaming travels through the fluidic channel, the laser beam may be motioned controlled such that it continuously samples the sample, optionally interface, and reference fluidic regions (e.g. the laser beam is translated during the measurement such that the average location of the interrogation region during laser motion scanning travels down the channel at the same rate as the fluidic boundary. In this manner, measurement samples are taken at multiple locations in the channel as the fluid travels down the channel. The traveling laser beam motion may be performed in 1 or 2 dimensions (i.e. down and across the channel)

The fluid boundary is in motion with respect to the channel, and the motion modulation signal includes a component that results in a translation of the interrogation region correlated to the motion of the fluidic boundary region.

Those versed in the art will recognized that the various embodiments of the fluid control and sensing techniques of this invention may also apply to non-optical techniques of measurement where it may be advantageous to compare a sample and reference. Examples may include conductivity measurements using electrodes or inductive loops, calorimetry, and pH. In such an example, the interrogation may not be optical but instead is determined by the detection mechanism's interaction with the fluids, such as the electrical or magnetic path when measuring conductivity.

While various embodiments have been particularly shown and described, it will be understood by those skilled in the art that various changes in form and details may be made therein without departing from the scope of the invention as defined by the appended claims.

What is claimed is:

1. A fluid analyzer, comprising:
an optical source and an optical detector defining a beam path of an optical beam;
a fluid flow cell disposed on the beam path defining an interrogation region in a fluid channel in the fluid flow cell in which the optical beam interacts with fluids;
one or more flow-control devices configured to conduct a particle in a fluid through the fluid channel;
a motion system configured to move the interrogation region relative to the fluid channel in response to a motion signal; and
a controller configured and operative (1) to generate the motion signal having a time-varying characteristic, (2) to sample an output signal from the optical detector at a first interval of the motion signal during which the interrogation region substantially contains the particle and at a second interval of the motion signal during which the interrogation region contains a region substantially not containing the particle, thereby generating corresponding output signal samples, and (3) to determine from the output signal samples a measurement value indicative of an optically measured characteristic of the particle.

2. The fluid analyzer of claim 1, including a feedback system having a measurement system for detecting the location and motion of the particle within the fluidic channel, and wherein the detecting is used to calculate a new operating parameter of the controller.

3. The fluid analyzer of claim 2, wherein during operation the fluid is in motion and the interrogation region is moved in the direction of fluid motion, and wherein the controller is configured and operative to (1) generate a second motion signal having a time-varying characteristic, (2) to sample a second output signal from the optical detector at a first interval of the second motion signal during which the interrogation region substantially contains the particle and at a second interval of the second motion signal during which the interrogation region contains a region substantially not containing the particle, thereby generating corresponding second output signal samples, and (3) to determine from the second output signal samples a measurement value indicative of an optically measured characteristic of the particle.

4. The fluid analyzer of claim 1, wherein a future motion signal is generated in response to the measurement value.

5. The fluid analyzer of claim 1, wherein the fluid contains multiple particles in the interrogation region and the measurement value is indicative of an optically measured characteristic of the multiple particles.

6. The fluid analyzer of claim 1, wherein the fluid is a first fluid, and wherein the one or more flow-control devices is configured to conduct a second fluid in the fluid channel, and the motion signal is operative to position the interrogation region in the first fluid during the first interval and in the second fluid during the second interval.

7. The fluid analyzer of claim 6, wherein the first and second fluids are flowing in the fluid channel during the first and second intervals respectively.

8. The fluid analyzer of claim 7, wherein the first fluid flow is terminated between the first and second intervals respectively.

9. The fluid analyzer of claim 6, wherein a flow of the first or second fluid in the fluid channel is terminated prior to the first or second interval.

10. The fluid analyzer of claim 6, wherein the motion control device conducts a third fluid into the fluid channel, the third fluid spatially between the first and second fluid.

11. The fluid analyzer of claim 6, wherein the volume of first fluid consumed in the measurement is materially less than the volume of the second fluid.

12. The fluid analyzer of claim 1, wherein the interrogation region in the second interval contains a region containing a second particle.

13. The fluid analyzer of claim 12, wherein the first interval interrogation region contains more or fewer particles than the second interval interrogation region.

14. The fluid analyzer of claim 13, wherein the measurement value is indicative of the difference in optical signal sampled at the detector in the first and second interval.

15. The fluid analyzer of claim 12, wherein the first or second interval interrogation region contains a known distribution of particles.

16. The fluid analyzer of claim 1, wherein the optical beam signal incident on the detector has been spatially filtered for the purpose of detecting scattered optical signal.

17. The fluid analyzer of claim 1, wherein the optical beam signal incident on the detector has been spatially filtered for the purpose of removing scattered optical signal.

18. The fluid analyzer of claim 1, wherein measurement values are determined at multiple wavelengths of optical light to estimate particle size.

19. The fluid analyzer of claim 1, wherein the optically measured characteristic of the particle is an optically measured characteristic of an interaction of the particle and the fluid.

20. The fluid analyzer of claim 1, wherein the optically measured characteristic of the particle is an optically measured characteristic of an interaction of the particle and the optical beam.

21. The fluid analyzer of claim 1, wherein the optically measured characteristic of the particle is an optically measured characteristic of an interaction of the particle and the fluid flow cell.

22. The fluid analyzer of claim 1, wherein the fluid channel supports multiple simultaneous optical beams and interrogation regions, and the multiple interrogation regions are sampled by the controller.

23. The fluid analyzer of claim 1, wherein the controller is operative to adjust the position, size or shape of the interrogation region.

24. The fluid analyzer of claim 23, wherein a position, size or shape of the interrogation region is determined by the controller in a feedback loop that uses the measurement value.

25. The fluid analyzer of claim 1, wherein the first fluid contains a particle with a known value of an optically measured characteristic, and (1) a measurement value of the particle characteristic and (2) the known value for of an optically measured characteristic are used in determining an optically measured characteristic of the particle.

26. The fluidic analyzer of claim 1, wherein the first fluid contains a dissolved analyte, and measurement value at multiple wavelengths of the optical beam are used to determine a measurement value of the analyte.

27. A fluidic analyzer of claim 1, wherein the measured values at multiple wavelengths of the optical beam are used to estimate particle chemical composition and size.

28. The fluid analyzer of claim 1, wherein the motion signal provides for rapid spatial scanning of the interrogation region over dimensions on the order of the particle size and slower spatial scanning over dimensions substantially greater than the particle size.

29. The fluid analyzer of claim 28, wherein the rapid spatial scanning is a 1-dimensional scan and the slower spatial scanning is a 2-dimensional scan.

30. The fluid analyzer of claim 28, wherein the slower spatial scanning is in a region with a known distribution of included particles or droplets.

31. The fluid analyzer of claim 1, further comprising a channel imaging device with an output signal used by the controller for determining the motion signal and the first and second intervals.

32. The fluid analyzer of claim 1, further comprising a transducer with a transducer output signal used by the controller and indicative of the presence of the particle and its position in the channel.

33. The fluid analyzer of claim 1, wherein the particle is adhering to a surface of the fluid channel during the first interval.

34. The fluid analyzer of claim 1, wherein both transmission and emission detection are performed, where transmission is used to detect immiscible analytes and infrared emission is used to detect or image non-immiscible analytes.

* * * * *